(12) United States Patent
Sandberg et al.

(10) Patent No.: US 7,666,842 B2
(45) Date of Patent: Feb. 23, 2010

(54) ELASTIN PEPTIDE ANALOGS AND USES THEREOF

(75) Inventors: Lawrence B Sandberg, Colton, CA (US); Thomas F Mitts, Visalia, CA (US)

(73) Assignee: Connective Tissue Imagineering, LLC, Visalia, CA (US)

( * ) Notice: Subject to any disclaimer, the term of this patent is extended or adjusted under 35 U.S.C. 154(b) by 42 days.

(21) Appl. No.: 10/946,436

(22) Filed: Sep. 21, 2004

(65) Prior Publication Data

US 2005/0059599 A1 Mar. 17, 2005

Related U.S. Application Data

(63) Continuation of application No. 09/580,156, filed on May 30, 2000, now Pat. No. 6,962,904, which is a continuation-in-part of application No. 09/039,308, filed on Mar. 13, 1998, now Pat. No. 6,069,129, application No. 10/946,436, which is a continuation of application No. 09/580,110, filed on May 30, 2000, now Pat. No. 6,809,075.

(51) Int. Cl.
  *A61K 38/07* (2006.01)
  *A61K 38/08* (2006.01)
  *C07K 5/00* (2006.01)
  *C07K 7/06* (2006.01)

(52) U.S. Cl. .............................. 514/16; 514/17; 514/18; 530/328; 530/329; 530/330

(58) Field of Classification Search ........................ None
  See application file for complete search history.

(56) References Cited

U.S. PATENT DOCUMENTS

| | | | |
|---|---|---|---|
| 4,118,480 A | 10/1978 | Williams | |
| 4,323,553 A | 4/1982 | Bouillon et al. | |
| 4,327,078 A | 4/1982 | Charlet et al. | |
| 4,381,294 A | 4/1983 | Bouillon et al. | |
| 4,474,763 A | 10/1984 | Lubowe | |
| 4,591,501 A | 5/1986 | Cioca | |
| 4,603,146 A | 7/1986 | Kligman | |
| 4,659,740 A | 4/1987 | Usher | |
| 4,668,476 A | 5/1987 | Bridgham et al. | |
| 4,816,513 A | 3/1989 | Bridgham et al. | |
| 4,877,805 A | 10/1989 | Kligman | |
| 4,891,227 A | 1/1990 | Thaman et al. | |
| 4,891,228 A | 1/1990 | Thaman et al. | |
| 4,963,656 A | 10/1990 | Mitani | |
| 4,983,382 A | 1/1991 | Wilmott et al. | |
| 5,017,691 A | 5/1991 | Lee | |
| 5,028,695 A | 7/1991 | Eckmayer et al. | |
| 5,079,003 A | 1/1992 | Scaffidi et al. | |
| 5,122,536 A | 6/1992 | Perricone | |
| 5,140,043 A | 8/1992 | Darr et al. | |
| 5,223,420 A | 6/1993 | Rabaud et al. | |
| 5,358,934 A | 10/1994 | Borovsky | |
| 5,503,825 A | 4/1996 | Lane | |
| 5,523,291 A | 6/1996 | Janzen et al. | |
| 5,587,396 A | 12/1996 | Smith | |
| 5,643,949 A | 7/1997 | Van Scott et al. | |
| 5,648,209 A | 7/1997 | Avrameas et al. | |
| 5,726,040 A | 3/1998 | Ensley et al. | |
| 5,736,537 A | 4/1998 | Gubernick et al. | |
| 5,770,697 A | 6/1998 | Ferrari et al. | |
| 5,776,441 A | 7/1998 | Scancarella et al. | |
| 5,801,192 A | 9/1998 | Dumas et al. | |
| 5,945,409 A | 8/1999 | Crandall et al. | |
| 5,948,418 A | 9/1999 | Maes et al. | |
| 6,025,347 A | 2/2000 | Gubernick et al. | |
| 6,069,129 A | 5/2000 | Sandberg et al. | |
| 6,586,006 B2 * | 7/2003 | Roser et al. | ........... 424/484 |

FOREIGN PATENT DOCUMENTS

| | | |
|---|---|---|
| JP | 08/225594 | 3/1993 |
| WO | WO 94/08588 A1 | 4/1994 |
| WO | WO 96/35428 A1 | 11/1996 |
| WO | WO 98/47921 | 10/1998 |
| WO | WO 99/45941 | 9/1999 |
| WO | WO 00/28996 | 5/2000 |

OTHER PUBLICATIONS

Mulchahey et al. Cellular and Molecular Life Sciences (1999), 55(4), 653-662.*
Database Medline, PMID: 8412988. Price et al. Valyl-alanyl-prolyl-glycine (VAPG) serves as a quantitative marker for human elastins. Matrix (Stuttgart) (1993), 13(4), 307-11. See abstract.*
Blankenship, J.W. et al., "Oxysterol Incorporation Into Rat Aorta Resulting in Elastin Compositional Changes"; Lipids; vol. 26, No. 5, pp. 381-384; 1991.
Database CAPLUS, AN 107:54378, Raju, K. et al., Primary Structure of Bovine Elastin A, B, and C Deduced From the Sequences of cDNA clones, J. Biol. Chem., . . . 262(12), pp. 5755-5762, 1987.
Database CAPLUS, AN 107:191131, Charten et al., "QSAR for Peptide Bioactivities. Further Studies"; Pharmacochem. Libr., vol. 10, pp. 285-290, 1987.
Database CAPLUS, AN 108:167920, Bayer et al., Z. Naturforsch., C. Biosci, 42 (4), pp. 455-460, 1987.
Database CAPLUS, AN 115:65185, Doi, R. et al., "Effects of Synthetic Human Pancreastatin on Pancreatic Secretion an dblood Flow in Rats and Dogs", Peptides, . . . vol. 12(3), pp. 449-502, 1991.
Database CAPLUS, DN 122:102414, Bisaccia et al., Int, J. Pept. Res., 44, pp. 332-341, Apr. 1994.
Database CAPLUS, DN 127:219499, Morrelli et al. J. Pept. Res., 49(6), pp. 429-499, Jun. 1997.

(Continued)

Primary Examiner—Michael Borin
(74) Attorney, Agent, or Firm—Benesch Friediander Coplan & Aronoff LLP

(57) ABSTRACT

Compositions used to enhance the elasticity and/or appearance of tissue are described. The compositions include peptides and/or peptide-like compounds and combinations thereof having low molecular weights and which substantially correspond to sequences found in elastin. The compositions may be applied to human skin in a cosmetic or therapeutic formulation and may result in enhanced elasticity and turgor of the skin.

25 Claims, 5 Drawing Sheets

OTHER PUBLICATIONS

Database CAPLUS, 129:187343, Lograno, M. et al., "Identification of Elastin Peptides with Vasorelaxant Activity on Rat Thoracic Aorta", Int. J. Biochem. Cell Biol, . . . vol. 30, pp. 497-503, 1998.

Ferrance, J., Examiner's First Report on Patent Application No. 30854/99 by Connective Tissue Imagineering LLC, 2001.

Gibson, M.A. et al., "Further Characterization of Proteins Associated with Elastic Fiber Microfibrils Including the Molecular Cloning of MAGP-2 (MP25)"; The Journal of . . . Biological Chemistry; vol. 271, No. 2, pp. 1096-1103, Jan. 12, 1996.

Heiber, A.D. et al., "Detection of Elastin in the Human Fetal Membrane: Proposed Molecular Basis for Elasticity"; Placenta; vol. 18, pp. 301-312; 1997.

Hunninghake et al., Science, 212, pp. 925-927, May 1981.

Price, L.S.C. et al., Valyl-Alanyl-Prolyl-Glycine (VAPG) Services as a Quantative Marker for Human Elastins; Matrix; vol. 13, pp. 307-311; 1993.

Sandberg, L.B et al., "Quantitation of Elastin Through Measurement of Its Pentapeptide Content"; Biochemical and Biophysical Research Communications; vol. 136, No. 2, . . . pp. 672-678, Apr. 29, 1986.

Sandberg, L.B. et al., "Quantitation of Elastin in Tissues and Culture: Problems Related to the Accurate Measurement of Small Amounts of Elastin With Special Emphasis on . . . the Rat"; Connective Tissue Research; vol. 25, p. 139-148; 1990.

Sandberg, L.B. et al., "Structural Guidelines for an Acceptable Elastin and Tropoelastin: Application Towards Quantitation of Elastin Accumulation in Tissue Culture"; . . . Elastin: Chemical and Biological Aspects (Reprinted); pp. 22-24; 1990.

Database Caplus, DN 113:1980321. WO 8909787; Registry No. 129393-50-6.

Connective Tissue Imagineering, LLC v. Thomas F. Mitts - Declaration of Lucy Miller .

Apr. 30, 1992 invoice from Protein Preparatons, Inc. to Images Int. for purchase of Elastin E91.

Description of Elastin E91 from Protein Preparations, Inc. dated Apr. 30, 1992.

* cited by examiner

SEQUENCE LISTING

<160> NUMBER OF SEQ ID NOS: 75

<210> SEQ ID NO 1

```
<211> LENGTH: 3
<212> TYPE: PRT
<213> ORGANISM: Homo sapiens

<400> SEQUENCE: 1

Ala Val Gly
1

<210> SEQ ID NO 2
<211> LENGTH: 4
<212> TYPE: PRT
<213> ORGANISM: Homo sapiens

<400> SEQUENCE: 2

Val Gly Ala Gly
1

<210> SEQ ID NO 3
<211> LENGTH: 3
<212> TYPE: PRT
<213> ORGANISM: Homo sapiens

<400> SEQUENCE: 3

Ile Gly Gly
1

<210> SEQ ID NO 4
<211> LENGTH: 2
<212> TYPE: PRT
<213> ORGANISM: Homo sapiens

<400> SEQUENCE: 4

Leu Gly
1

<210> SEQ ID NO 5
<211> LENGTH: 4
<212> TYPE: PRT
<213> ORGANISM: Homo sapiens

<400> SEQUENCE: 5

Ile Gly Ala Gly
1

<210> SEQ ID NO 6
<211> LENGTH: 3
<212> TYPE: PRT
<213> ORGANISM: Homo sapiens

<400> SEQUENCE: 6

Leu Gly Gly
1

<210> SEQ ID NO 7
<211> LENGTH: 4
<212> TYPE: PRT
<213> ORGANISM: Homo sapiens

<400> SEQUENCE: 7

Val Ala Pro Gly
1

<210> SEQ ID NO 8
<211> LENGTH: 4
<212> TYPE: PRT
<213> ORGANISM: Homo sapiens
```

```
<400> SEQUENCE: 8

Leu Gly Pro Gly
1

<210> SEQ ID NO 9
<211> LENGTH: 4
<212> TYPE: PRT
<213> ORGANISM: Homo sapiens

<400> SEQUENCE: 9

Leu Gly Ala Gly
1

<210> SEQ ID NO 10
<211> LENGTH: 4
<212> TYPE: PRT
<213> ORGANISM: Homo sapiens

<400> SEQUENCE: 10

Val Gly Pro Gly
1

<210> SEQ ID NO 11
<211> LENGTH: 4
<212> TYPE: PRT
<213> ORGANISM: Homo sapiens

<400> SEQUENCE: 11

Phe Gly Pro Gly
1

<210> SEQ ID NO 12
<211> LENGTH: 4
<212> TYPE: PRT
<213> ORGANISM: Homo sapiens

<400> SEQUENCE: 12

Val Gly Pro Gln
1

<210> SEQ ID NO 13
<211> LENGTH: 3
<212> TYPE: PRT
<213> ORGANISM: Homo sapiens

<400> SEQUENCE: 13

Leu Gly Ala
1

<210> SEQ ID NO 14
<211> LENGTH: 4
<212> TYPE: PRT
<213> ORGANISM: Homo sapiens

<400> SEQUENCE: 14

Val Gly Pro Ala
1

<210> SEQ ID NO 15
<211> LENGTH: 4
<212> TYPE: PRT
<213> ORGANISM: Homo sapiens

<400> SEQUENCE: 15
```

```
Val Val Pro Gly
1

<210> SEQ ID NO 16
<211> LENGTH: 4
<212> TYPE: PRT
<213> ORGANISM: Homo sapiens

<400> SEQUENCE: 16

Ala Val Pro Gly
1

<210> SEQ ID NO 17
<211> LENGTH: 4
<212> TYPE: PRT
<213> ORGANISM: Homo sapiens

<400> SEQUENCE: 17

Val Val Pro Gln
1

<210> SEQ ID NO 18
<211> LENGTH: 6
<212> TYPE: PRT
<213> ORGANISM: Homo sapiens

<400> SEQUENCE: 18

Val Ala Ala Arg Pro Gly
1               5

<210> SEQ ID NO 19
<211> LENGTH: 7
<212> TYPE: PRT
<213> ORGANISM: Homo sapiens

<400> SEQUENCE: 19

Leu Gly Ala Gly Gly Ala Gly
1               5

<210> SEQ ID NO 20
<211> LENGTH: 4
<212> TYPE: PRT
<213> ORGANISM: Homo sapiens

<400> SEQUENCE: 20

Ala Ile Pro Gly
1

<210> SEQ ID NO 21
<211> LENGTH: 5
<212> TYPE: PRT
<213> ORGANISM: Homo sapiens

<400> SEQUENCE: 21

Leu Gly Pro Gly Gly
1               5

<210> SEQ ID NO 22
<211> LENGTH: 5
<212> TYPE: PRT
<213> ORGANISM: Homo sapiens

<400> SEQUENCE: 22

Ala Ala Ala Gln Ala
1               5
```

```
<210> SEQ ID NO 23
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Hydroxyproline

<400> SEQUENCE: 23

Val Gly Val Xaa Gly
1               5

<210> SEQ ID NO 24
<211> LENGTH: 5
<212> TYPE: PRT
<213> ORGANISM: Homo sapiens

<400> SEQUENCE: 24

Val Tyr Pro Gly Gly
1               5

<210> SEQ ID NO 25
<211> LENGTH: 6
<212> TYPE: PRT
<213> ORGANISM: Homo sapiens

<400> SEQUENCE: 25

Ile Gly Gly Val Gly Gly
1               5

<210> SEQ ID NO 26
<211> LENGTH: 6
<212> TYPE: PRT
<213> ORGANISM: Homo sapiens

<400> SEQUENCE: 26

Val Ala Pro Gly Val Gly
1               5

<210> SEQ ID NO 27
<211> LENGTH: 5
<212> TYPE: PRT
<213> ORGANISM: Homo sapiens

<400> SEQUENCE: 27

Leu Gly Val Gly Gly
1               5

<210> SEQ ID NO 28
<211> LENGTH: 4
<212> TYPE: PRT
<213> ORGANISM: Homo sapiens

<400> SEQUENCE: 28

Val Leu Pro Gly
1

<210> SEQ ID NO 29
<211> LENGTH: 5
<212> TYPE: PRT
<213> ORGANISM: Homo sapiens

<400> SEQUENCE: 29

Phe Arg Ala Ala Ala
1               5
```

```
<210> SEQ ID NO 30
<211> LENGTH: 6
<212> TYPE: PRT
<213> ORGANISM: Homo sapiens

<400> SEQUENCE: 30

Val Gly Gly Val Pro Gly
1               5

<210> SEQ ID NO 31
<211> LENGTH: 5
<212> TYPE: PRT
<213> ORGANISM: Homo sapiens

<400> SEQUENCE: 31

Phe Gly Pro Gly Gly
1               5

<210> SEQ ID NO 32
<211> LENGTH: 5
<212> TYPE: PRT
<213> ORGANISM: Homo sapiens

<400> SEQUENCE: 32

Val Gly Val Pro Gly
1               5

<210> SEQ ID NO 33
<211> LENGTH: 6
<212> TYPE: PRT
<213> ORGANISM: Homo sapiens

<400> SEQUENCE: 33

Val Leu Pro Gly Ala Gly
1               5

<210> SEQ ID NO 34
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Hydroxyproline

<400> SEQUENCE: 34

Val Gly Leu Xaa Gly
1               5

<210> SEQ ID NO 35
<211> LENGTH: 5
<212> TYPE: PRT
<213> ORGANISM: Homo sapiens

<400> SEQUENCE: 35

Leu Gly Val Gly Ala
1               5

<210> SEQ ID NO 36
<211> LENGTH: 4
<212> TYPE: PRT
<213> ORGANISM: Homo sapiens

<400> SEQUENCE: 36

Ala Phe Pro Gly
```

```
<210> SEQ ID NO 37
<211> LENGTH: 5
<212> TYPE: PRT
<213> ORGANISM: Homo sapiens

<400> SEQUENCE: 37

Ala Phe Pro Gly Ala
1               5

<210> SEQ ID NO 38
<211> LENGTH: 5
<212> TYPE: PRT
<213> ORGANISM: Homo sapiens

<400> SEQUENCE: 38

Val Gly Ile Pro Ala
1               5

<210> SEQ ID NO 39
<211> LENGTH: 6
<212> TYPE: PRT
<213> ORGANISM: Homo sapiens

<400> SEQUENCE: 39

Val Gly Gly Ile Pro Thr
1               5

<210> SEQ ID NO 40
<211> LENGTH: 7
<212> TYPE: PRT
<213> ORGANISM: Homo sapiens

<400> SEQUENCE: 40

Val Gly Val Gly Val Pro Gly
1               5

<210> SEQ ID NO 41
<211> LENGTH: 6
<212> TYPE: PRT
<213> ORGANISM: Homo sapiens

<400> SEQUENCE: 41

Leu Gly Pro Gly Val Gly
1               5

<210> SEQ ID NO 42
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: AMIDATION

<400> SEQUENCE: 42

Val Val Pro Gln
1

<210> SEQ ID NO 43
<211> LENGTH: 4
<212> TYPE: PRT
<213> ORGANISM: Homo sapiens
<220> FEATURE:
<221> NAME/KEY: MOD_RES
<222> LOCATION: (1)..(1)
```

```
<223> OTHER INFORMATION: ACETYLATION

<400> SEQUENCE: 43

Val Val Pro Gln
1

<210> SEQ ID NO 44
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 44

Gly Ala Val Val Pro Gln
1               5

<210> SEQ ID NO 45
<211> LENGTH: 5
<212> TYPE: PRT
<213> ORGANISM: Homo sapiens

<400> SEQUENCE: 45

Ala Val Val Pro Gln
1               5

<210> SEQ ID NO 46
<211> LENGTH: 6
<212> TYPE: PRT
<213> ORGANISM: Homo sapiens

<400> SEQUENCE: 46

Gly Ala Val Val Pro Gln
1               5

<210> SEQ ID NO 47
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION

<400> SEQUENCE: 47

Ala Val Val Pro Gln
1               5

<210> SEQ ID NO 48
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: AMIDATION

<400> SEQUENCE: 48

Gly Ala Val Val Pro Gln
1               5

<210> SEQ ID NO 49
```

```
<211> LENGTH: 6
<212> TYPE: PRT
<213> ORGANISM: Homo sapiens
<220> FEATURE:
<221> NAME/KEY: DISULFID
<222> LOCATION: (1)..(6)

<400> SEQUENCE: 49

Cys Val Val Pro Gln Cys
1               5

<210> SEQ ID NO 50
<211> LENGTH: 7
<212> TYPE: PRT
<213> ORGANISM: Homo sapiens
<220> FEATURE:
<221> NAME/KEY: DISULFID
<222> LOCATION: (1)..(7)

<400> SEQUENCE: 50

Cys Ala Val Val Pro Gln Cys
1               5

<210> SEQ ID NO 51
<211> LENGTH: 8
<212> TYPE: PRT
<213> ORGANISM: Homo sapiens
<220> FEATURE:
<221> NAME/KEY: DISULFID
<222> LOCATION: (1)..(8)

<400> SEQUENCE: 51

Cys Gly Ala Val Val Pro Gln Cys
1               5

<210> SEQ ID NO 52
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: copper as a cheating agent to form a cyclic
      structure between terminal amino acids

<400> SEQUENCE: 52

Cys Val Val Pro Gln Cys
1               5

<210> SEQ ID NO 53
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: copper as a cheating agent to form a cyclic
      structure between terminal amino acids

<400> SEQUENCE: 53

Cys Ala Val Val Pro Gln Cys
1               5

<210> SEQ ID NO 54
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
```

-continued

```
<223> OTHER INFORMATION: copper as a cheating agent to form a cyclic
      structure between terminal amino acids

<400> SEQUENCE: 54

Cys Gly Ala Val Val Pro Gln Cys
1               5

<210> SEQ ID NO 55
<211> LENGTH: 4
<212> TYPE: PRT
<213> ORGANISM: Homo sapiens

<400> SEQUENCE: 55

Val Val Pro Asn
1

<210> SEQ ID NO 56
<211> LENGTH: 5
<212> TYPE: PRT
<213> ORGANISM: Homo sapiens

<400> SEQUENCE: 56

Ala Val Val Pro Asn
1               5

<210> SEQ ID NO 57
<211> LENGTH: 6
<212> TYPE: PRT
<213> ORGANISM: Homo sapiens

<400> SEQUENCE: 57

Gly Ala Val Val Pro Asn
1               5

<210> SEQ ID NO 58
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION

<400> SEQUENCE: 58

Ala Val Val Pro Asn
1               5

<210> SEQ ID NO 59
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: AMIDATION

<400> SEQUENCE: 59

Gly Ala Val Val Pro Asn
1               5

<210> SEQ ID NO 60
<211> LENGTH: 6
<212> TYPE: PRT
<213> ORGANISM: Homo sapiens
<220> FEATURE:
<221> NAME/KEY: DISULFID
<222> LOCATION: (1)..(6)
```

```
<400> SEQUENCE: 60

Cys Val Val Pro Asn Cys
1               5

<210> SEQ ID NO 61
<211> LENGTH: 7
<212> TYPE: PRT
<213> ORGANISM: Homo sapiens
<220> FEATURE:
<221> NAME/KEY: DISULFID
<222> LOCATION: (1)..(7)

<400> SEQUENCE: 61

Cys Ala Val Val Pro Asn Cys
1               5

<210> SEQ ID NO 62
<211> LENGTH: 8
<212> TYPE: PRT
<213> ORGANISM: Homo sapiens
<220> FEATURE:
<221> NAME/KEY: DISULFID
<222> LOCATION: (1)..(8)

<400> SEQUENCE: 62

Cys Gly Ala Val Val Pro Asn Cys
1               5

<210> SEQ ID NO 63
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: copper as a cheating agent to form a cyclic
      structure between terminal amino acids

<400> SEQUENCE: 63

Cys Val Val Pro Asn Cys
1               5

<210> SEQ ID NO 64
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: copper as a cheating agent to form a cyclic
      structure between terminal amino acids

<400> SEQUENCE: 64

Cys Ala Val Val Pro Asn Cys
1               5

<210> SEQ ID NO 65
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: copper as a cheating agent to form a cyclic
      structure between terminal amino acids

<400> SEQUENCE: 65

Cys Gly Ala Val Val Pro Asn Cys
1               5
```

```
<210> SEQ ID NO 66
<211> LENGTH: 8
<212> TYPE: PRT
<213> ORGANISM: Homo sapiens

<400> SEQUENCE: 66

Leu Gly Ala Gly Gly Ala Gly Val
1               5

<210> SEQ ID NO 67
<211> LENGTH: 9
<212> TYPE: PRT
<213> ORGANISM: Homo sapiens

<400> SEQUENCE: 67

Leu Gly Ala Gly Gly Ala Gly Val Leu
1               5

<210> SEQ ID NO 68
<211> LENGTH: 8
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: AMIDATION

<400> SEQUENCE: 68

Leu Gly Ala Gly Gly Ala Gly Val
1               5

<210> SEQ ID NO 69
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 69

Leu Gly Ala Gly Gly Ala Gly Val Leu
1               5

<210> SEQ ID NO 70
<211> LENGTH: 9
<212> TYPE: PRT
<213> ORGANISM: Homo sapiens
<220> FEATURE:
<221> NAME/KEY: DISULFID
<222> LOCATION: (1)..(9)

<400> SEQUENCE: 70

Cys Leu Gly Ala Gly Gly Ala Gly Cys
1               5

<210> SEQ ID NO 71
<211> LENGTH: 10
<212> TYPE: PRT
<213> ORGANISM: Homo sapiens
<220> FEATURE:
<221> NAME/KEY: DISULFID
<222> LOCATION: (1)..(10)

<400> SEQUENCE: 71

Cys Leu Gly Ala Gly Gly Ala Gly Val Cys
1               5                   10
```

```
<210> SEQ ID NO 72
<211> LENGTH: 11
<212> TYPE: PRT
<213> ORGANISM: Homo sapiens
<220> FEATURE:
<221> NAME/KEY: DISULFID
<222> LOCATION: (1)..(11)

<400> SEQUENCE: 72

Cys Leu Gly Ala Gly Gly Ala Gly Val Leu Cys
1               5                   10

<210> SEQ ID NO 73
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: copper as a cheating agent to form a cyclic
      structure between terminal amino acids

<400> SEQUENCE: 73

Cys Leu Gly Ala Gly Gly Ala Gly Cys
1               5

<210> SEQ ID NO 74
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: copper as a cheating agent to form a cyclic
      structure between terminal amino acids

<400> SEQUENCE: 74

Cys Leu Gly Ala Gly Gly Ala Gly Val Cys
1               5                   10

<210> SEQ ID NO 75
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: copper as a cheating agent to form a cyclic
      structure between terminal amino acids

<400> SEQUENCE: 75

Cys Leu Gly Ala Gly Gly Ala Gly Val Leu Cys
1               5                   10
```

ELASTIN PEPTIDE ANALOGS AND USES THEREOF

CROSS REFERENCE TO RELATED APPLICATIONS

This application claims priority from and is a continuation of, pursuant to 35 U.S.C. § 120, U.S. patent application Ser. No. 09/580,156, filed May 30, 2000, which is a continuation-in-part of U.S. Pat. No. 6,069,129, filed Mar. 13, 1998, and U.S. patent application Ser. No. 09/580,110, filed May 30, 2000, all of which are incorporated herein by reference.

BACKGROUND OF THE INVENTION

Over time, skin and other tissues may lose some of its texture, softness, resilience and the like. The skin may then have a less desirable appearance. The loss or decrease of these and other characteristics may come about from factors such as loss of moisture from the skin, changes in the molecules that are part of the skin and others. Attempts have been made to revitalize tissues such as skin. One method is to attempt to add back some of the factors thought to be decreased or lost from skin. Such attempts may not always be successful. For example, attempts to moisturize skin by topical application of moisturizers may not improve skin appearance if this is due to factors other than dryness. Also, agents added to the skin may not always be in a form that can reach and/or be absorbed by the particular area of the tissue that is in need of the agent.

BRIEF DESCRIPTION OF THE DRAWINGS

The accompanying drawings or figures, which are incorporated in and constitute a part of the specification, illustrate various example compositions, data, structures and so forth which, together with the detailed description given below, serve to describe the example embodiments of the claimed subject matter. The drawings are for the purposes of illustrating the preferred and alternate embodiments and are not to be construed as limitations.

DETAILED DESCRIPTION

Figure 1:
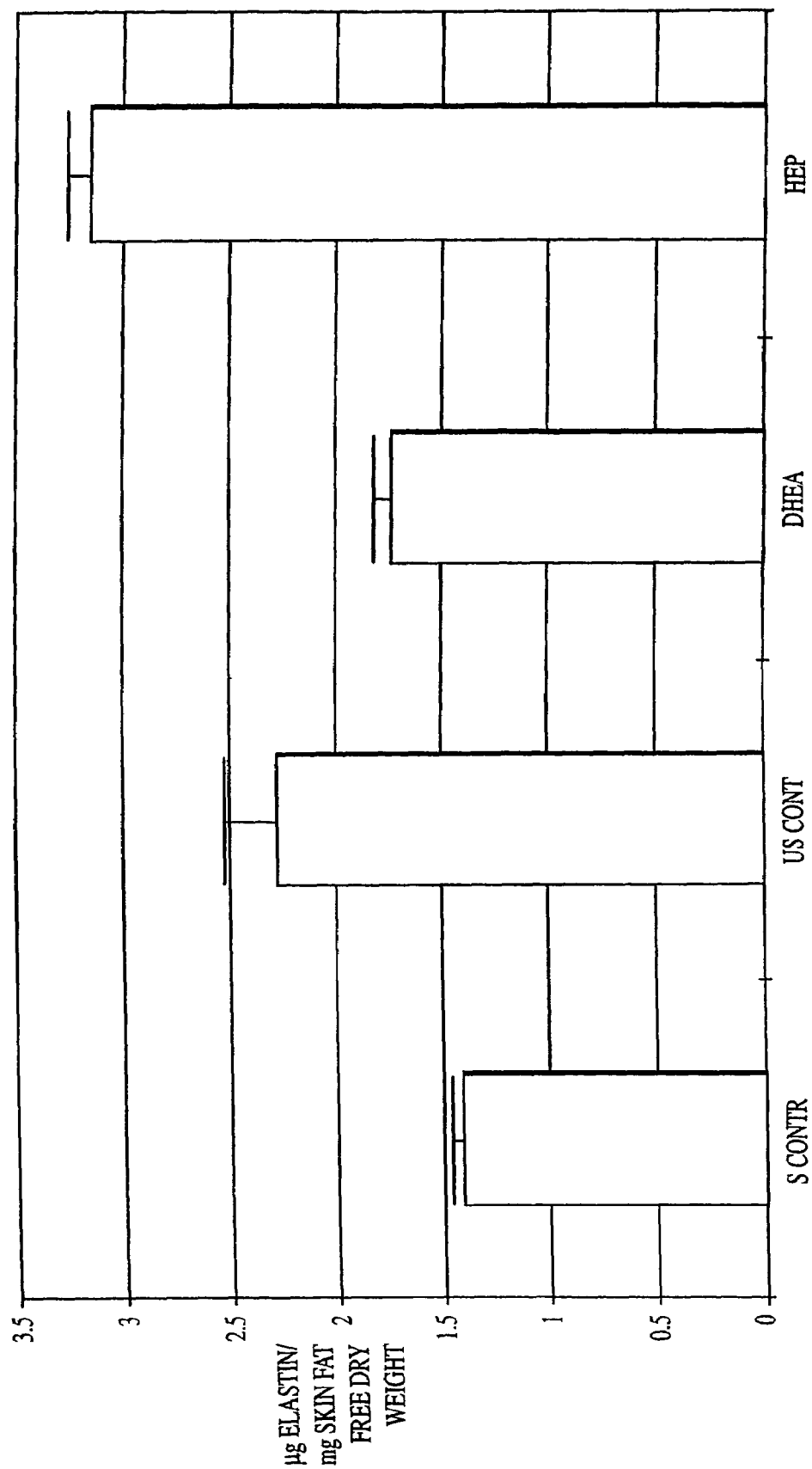
FIG. 1 illustrates the results of an example experiment in a bar graph, showing increased elastin production in response to application of various compounds to mammalian skin.

This application describes compositions containing one or more peptides and methods for using the compositions. The peptides of the composition may correspond to, be analogous to, or are substantially homologous, with portions of elastin. The elastin may come from a variety of different organisms. The compositions may be pharmaceutical, therapeutic, and/or cosmetic in nature. The compositions may be used for treating tissue, skin for example. The compositions and methods may be useful in increasing one or more of functionality, elasticity, tone, turgor, and/or appearance of tissue.

The following includes definitions of selected terms employed herein. The definitions include various examples and/or forms of components that fall within the scope of a term and that may be used for implementation. The examples are not intended to be limiting. Both singular and plural forms of terms maybe within the definitions.

As used herein, "amino acid" refers to a carboxylic acid having an amino group attached to the alpha carbon atom. Such amino acids may be naturally occurring L amino acids, unless otherwise specifically indicated. The commonly used one- and three-letter abbreviations for amino acids are use herein (Lehninger, 1975, in Biochemistry, 2 nd edition, Worth Publishers, New York, pp. 71-92).

As used herein, "peptide bond" refers to the chemical bond formed between the alpha-amino group of one amino acid and the alpha-carboxyl group of a second amino acid (i.e., amide linkages).

As used herein, "protein" describes a linear polymer or sequence of amino acids, joined by peptide bonds. Such proteins may be naturally occurring, meaning that they can be isolated from cells or tissues.

As used herein, "peptide" also refers to a linear polymer or sequence of amino acids, joined by peptide bonds. Peptides, however, may not be naturally occurring in that they may not be isolated from cells or tissues. Instead, peptides may be obtained from hydrolysis of some of the peptide bonds of a protein. Peptides may also be obtained by chemical synthesis in which peptide bonds are formed between amino acids, or between amino acids and peptides. Herein, peptides may be from 2 amino acids long to about 50 amino acids long.

Proteins and peptides are generally defined by a linear sequence of amino acids. An amino acid sequence generally has a free amino group at the N-terminal end and a free carboxyl group at the C-terminal end. In the notation used herein to describe the amino acid sequence of a protein or peptide, the left-hand end of an amino acid sequence denotes the N-terminal end, and the right-hand end denotes the C-terminal end. Other types of peptides are disclosed in U.S. Pat. No. 6,506,731 to Sandberg and Mitts, which is incorporated herein by reference.

Additionally, the term "elastin peptide fragment" in either singular or plural form refers herein to the fact that the peptide or amino acid sequence being discussed, corresponds to, is the biological equivalent of, is analogous with, or is substantially homologous with, a portion of elastin. The term "elastin peptide fragment" is not meant to convey any meaning regarding the source or starting material or method of arriving at the elastin peptide fragment.

As used herein, "modified peptides" refers to peptides that have one or more of the following: i) one or more amino acids that are non-naturally occurring, ii) one or more D-amino acids, and iii) one or more non-hydrolyzable bonds between adjacent amino acids. Additionally, modified peptides include cyclized peptides.

As used herein, "carrier" refers to an organic or inorganic ingredient, natural or synthetic, with which the peptides can be combined to facilitate administration.

As used herein, "pharmaceutically-acceptable carrier" refers to one or more compatible solid or liquid filler, diluents or encapsulating substances which are suitable for administration into a human or other animal. The components comprising these carriers are capable of being commingled with the peptides, and with each other, in a manner such that there is no interaction which would substantially impair the desired pharmaceutical efficacy.

As used herein, the term "subject" or "patient" means any mammal, including humans, in which elastin is utilized for proper tissue function or appearance. The methods herein for use contemplate prophylactic, cosmetic, and curative use.

As used herein, the term "tissue" refers to any aggregation of similarly specialized cells which are united in the performance of a particular function. The term "tissue", as usually used herein, refers to tissue which includes elastin as part of its preferred structure and/or function. The term "skin" may be encompassed by the term "tissue" but specifically means the outer integument or covering of the body, including the dermis and the epidermis which rests upon subcutaneous tissue.

As used herein, "providing", when used in conjunction with a therapeutic, pharmaceutical, or cosmetic means to administer an agent into or onto a target tissue or to administer a therapeutic to a patient whereby the therapeutic positively impacts the tissue to which it is targeted (either in a prophylactic, curative or cosmetic manner). Thus, as used herein, the term "providing", when used in conjunction with elastin peptide fragment, may include, but is not limited to, providing an elastin peptide fragment into or onto the target tissue; providing an elastin peptide fragment systemically to a patient by, e.g., intravenous injection whereby the therapeutic agent reaches the target tissue; providing an elastin peptide fragment in the form of the encoding sequence thereof to the target tissue (e.g., by so-called gene-therapy techniques) whereby the elastin peptide fragment is expressed within the target tissue. Details on techniques for formulation and administration of pharmaceuticals may be found in Remington's Pharmaceutical Sciences (Mack Publishing Co, Easton Pa.). Although local topical delivery may be used, there are other acceptable means of delivery, for example: oral, parenteral, aerosol, intramuscular, subcutaneous, transcutaneous, intamedullary, intrathecal, intraventricular, intravenous, intraperitoneal, intranasal administration and others.

As used herein, the term "therapeutic" means an agent utilized to treat, combat, ameliorate, prevent or improve a condition or disease of a patient. A particular condition treated in the present invention may be deficient elastin in a particular tissue, that is, a need in the tissue for more elastin. As it applies to skin, "therapy" may be measured by turgor, tone, appearance, degree of wrinkles, and youthfulness. As the term applies to blood vessels, it may be measured by the degree of elasticity or proper vasomotor response (vasodilatation/vasoconstriction) of the vessel. Accordingly, therapeutic treatment of blood vessels may have implications in diseases associated with visco-elasticity, including hypertension, arteriosclerosis, angina, angiogenesis, myocardial infarction, coronary thrombosis, restenosis post angioplasty, and chronic obstructive pulmonary disease.

As used herein, the term "cosmetic" refers to a beautifying substance or preparation which preserves, restores, bestows, simulates, or enhances the appearance of bodily beauty, specifically as it relates to the appearance of tissue or skin.

Preparation of Elastin Peptides—Digestion

Generally, the peptides described herein are from or have an amino acid sequence that is found within one or more forms of elastin. One way of obtaining such peptides is to use elastin and to hydrolyze some of the peptide bonds therein. The elastin used in such hydrolysis or digestion procedures may come from a variety of sources. One example source of elastin is *ligamentum nuchae,* a posterior ligament of the cervical spine (i.e., back of the neck). *Ligamentum nuchae* contains large amounts of elastin, especially in proportion to the amount of collagen. The *ligamentum nuchae* may be cleaned first using a procedure similar to that disclosed in U.S. Pat. No. 5,028,695, the cleaning portion of which is incorporated herein by reference thereto. Other example sources of elastin are other ligaments, tendons, connective tissue and other tissue. The arteries and lungs, and other animal tissue, especially those which have significant amounts of elastin, can be used. Also, elastin from different sources, or elastin and collagen from the same or different sources could be mixed together to produce a particular advantageous mix suitable for digestion or hydrolytic cleavage. Synthetic sources of elastin may also be used.

Elastin peptides may be obtained from the elastin in a variety of ways. Generally, this is done by breaking or cleaving some of the peptide bonds between certain pairs of amino acids in the protein. A variety of different substances may be used. Generally, one or more enzymes may be used. Such enzymes may digest or hydrolyze some of the peptide bonds in the protein. Such enzymes may be called proteases. Generally, such enzymes partially or selectively hydrolyze the peptide bonds. For example, enzymes may have the ability to hydrolyze every peptide bond within elastin. To achieve partial hydrolysis, the enzymatic reaction with these enzymes is somehow limited so that some, but not all, peptide bonds are cleaved. In one example, the protease reaction may be limited by inhibiting or stopping the reaction before the protease has cleaved all of the peptide bonds. In another example, enzymes may have the ability to hydrolyze certain peptide bonds but not others. Generally, the specificity of such enzymes is dependent on the amino acid sequences in the protein. Enzymes which are examples of enzymes that may be used for hydrolysis reactions include trypsin, chymotrypsin, pepsin, thermolysin, Proteinase K, elastase and others. Non-enzymatic substances may include compounds such as cyanogen bromide.

Preparation of Elastin Peptides—Synthesis

A wide variety of different techniques are known for making peptide segments, and any such method can be used in making the inventive peptides.

Synthesis of peptides may involve chemical synthesis and may include subsequent treatment under oxidizing conditions appropriate to obtain the native conformation, that is, the correct disulfide bond linkages. This may be accomplished using known methods (e.g., Kelly and Winkler, 1990, in Genetic Engineering Principles and Methods, vol. 12, J. K. Setlow editor, Plenum Press, New York, pp. 1-19; Stewart and Young, 1984, Solid Phase Peptide Synthesis, Pierce Chemical Co., Rockford, Ill.). One such method is described below.

Peptides of the invention may be prepared using solid phase synthesis (Merrifield, 1964, J Amer Chem Soc, 85:2149; Houghten, 1985, Proc Natl Acad Sci USA, 82:5131-5). Solid phase synthesis can begin at the C-terminus of the putative peptide by coupling a protected amino acid to a suitable resin. In this synthesis, the carboxyl terminal amino acid, with its α-amino group suitably protected, may be coupled to a chloromethylated polystyrene resin. After removal of the α-amino protecting group with, for example, trifluoroacetic acid (TFA) in methylene chloride and neutralizing in, for example TEA, the next cycle in the synthesis may proceed.

The remaining α-amino- and, if necessary, side-chain-protected amino acids may then be coupled sequentially in the desired order by condensation to obtain an intermediate compound connected to the resin. Alternatively, some amino acids may be coupled to one another forming a peptide prior to addition of the peptide to the growing solid phase peptide chain. The condensation between two amino acids, or an amino acid and a peptide, or a peptide and a peptide may be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method, etc.), and Woodward reagent K method. In the case of elongating the peptide chain in the solid phase method, the peptide may be attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin may be used.

Generally common to chemical synthesis of peptides is the protection of the reactive side-chain R groups of the various amino acid moieties with suitable protecting groups at that site until the group is ultimately removed after the chain has been completely assembled. Also common is the protection of the α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the reactive amino side-chain groups of the various amino acid moieties may be exemplified by benzyloxycarbonyl (abbreviated Z), isonicotinyloxycarbonyl (iNOC), O-chlorobenzyloxycarbonyl [Z(NO$_2$)], p-methoxybenzyloxycarbonyl [Z(OMe)], t-butoxycarbonyl, (Boc), t-amyioxycarbonyl (Aoc), isobomyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

As protective groups for carboxy groups there may be exemplified, for example, benzyl ester (OBzl), cyclohexyl ester (Chx), 4-nitrobenzyl ester (ONb), t-butyl ester (Obut), 4-pyridylmethyl ester (OPic), and the like. It may be that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb) etc, and the hydroxyl group in the serine can be protected with benzyl, t-butyl, acetyl, tetrahydropyranyl etc.

Stewart and Young, supra, provides detailed information regarding procedures for preparing peptides.

After the desired amino acid sequence has been completed, the intermediate peptide may be removed from the resin support by treatment with a reagent, such as liquid HF and one or more thio-containing scavengers, which cleaves the peptide from the resin, and also cleaves all the remaining side-chain protecting groups. Following HF cleavage, the protein sequence can be washed with ether, transferred to a large volume of dilute acetic acid, and stirred at pH adjusted to about 8.0 with ammonium hydroxide.

Additionally, in order to avoid alkylation of residues in the peptide, (e.g., alkylation of methionine, cysteine, and tyrosine residues) a thio-cresol and cresol scavenger mixture may be used. The resin may be washed with ether, and immediately transferred to a large volume of dilute acetic acid to solubilize and minimize intermolecular cross-linking. A 250 μM peptide concentration can be diluted in about 2 liters of 0.1 M acetic acid solution. The solution can then be stirred and its pH adjusted to about 8.0 using ammonium hydroxide. Upon pH adjustment, the peptide may take its desired conformational arrangement.

Kunitz domains (i.e., functional sites) may be made either by chemical synthesis, described above, or by semisynthesis. The chemical synthesis or semisynthesis methods of making allow the possibility of modified amino acid residues to be incorporated. This has been carried out for Kunitz domains and related proteins as previously described (Beckmann, et al., 1988, Eur J Biochem, 176:675-82; Bigler, et al., 1993, Protein Sci, 2:786-99).

A general method for synthesizing peptides is described in U.S. Pat. No. 4,816,513, incorporated herein by reference thereto in its entirety, which describes a process for automatically constructing a polypeptide. Additionally, U.S. Pat. No. 4,668,476, incorporated herein by reference thereto in its entirety, also describes an apparatus for automatically constructing a polypeptide and a transfer system to transfer activated species from the activator system to the reaction vessel and to transfer amino acids, reagents, gases and solvents from one part of the apparatus to another. Generally, this synthesis process is conducted using Fmoc chemistry on automated solid phase synthesizers, (or in some cases by Boc chemistry). In most cases, the synthesized peptides would be purified by HPLC using reversed phase C4 and C18 columns. Alternate purification methods include ion exchange and gel filtration chromatography.

Separation, Purification and Identification of Peptides

Peptides from digestion or from synthesis may be purified from reaction components. One or more peptides may also be separated from one or more other peptides. Such methods and techniques for purification and/or separation are known in the art of chemistry, biological chemistry, and the like, for example. One method that may be used is high performance liquid chromatography (HPLC). A variety of other methods may be used.

Peptides may also be subjected to various methods for identifying the peptides (e.g., based on the amino acid sequence contained therein). A variety of methods may be used. In one example, chromatography may be used. In another method, the amino acid sequence of one or more of the peptides may be analyzed.

Peptide Identities

Table I is a list of peptide sequences, based on their amino acid sequences which, either alone or in combination, may exhibit desirable characteristics.

TABLE I

| SEQ # | PEPTIDE | MOL WT | NAME (N-to-C-terminal) |
|---|---|---|---|
| 1 | AVG | 245 | Alanine-Valine-Glycine |
| 2 | VGAG | 302 | Valine-Glycine-Alanine-Glycine |

TABLE I-continued

| SEQ # | PEPTIDE | MOL WT | NAME (N-to-C-terminal) |
|---|---|---|---|
| 3 | IGG | 302 | Isoleucine-Glycine-Glycine |
| 4 | LG | 188 | Leucine-Glycine |
| 5 | IGAG | 316 | Isoleucine-Glycine-Alanine-Glycine |
| 6 | LGG | 245 | Leucine-Glycine-Glycine |
| 7 | VAPG | 342 | Valine-Alanine-Proline-Glycine |
| 8 | LGPG | 342 | Leucine-Glycine-Proline-Glycine |
| 9 | LGAG | 316 | Leucine-Glycine-Alanine-Glycine |
| 10 | VGPG | 328 | Valine-Glycine-Proline-Glycine |
| 11 | FGPG | 376 | Phenylalanine-Glycine-Proline-Glycine |
| 12 | VGPQ | 399 | Valine-Glycine-Proline-Glutamine |
| 13 | LGA | 259 | Leucine-Glycine-Alanine |
| 14 | VGPA | 342 | Valine-Glycine-Proline-Alanine |
| 15 | VVPG | 370 | Valine-Valine-Proline-Glycine |
| 16 | AVPG | 342 | Alanine-Valine-Proline-Glycine |
| 17 | VVPQ | 441 | Valine-Valine-Proline-Glutamine |
| 18 | VAARPG | 569 | Valine-Alanine-Alanine-Arginine-Proline-Glycine |
| 19 | LGAGGAG | 501 | Leucine-Glycine-Alanine-Glycine-Glycine-Alanine-Glycine |
| 20 | AIPG | 356 | Alanine-Isoleucine-Proline-Glycine |
| 21 | LGPGG | 399 | Leucine-Glycine-Proline-Glycine-Glycine |
| 22 | AAAQA | 430 | Alanine-Alanine-Alanine-Glutamine-Alanine |
| 23 | VGVHypG | 444 | Valine-Glycine-Valine-Hydroxyproline-Glycine |
| 24 | VYPGG | 491 | Valine-Tyrosine-Proline-Glycine-Glycine |
| 25 | IGGVGG | 458 | Isoleucine-Glycine-Glycine-Valine-Glycine-Glycine |
| 26 | VAPGVG | 498 | Valine-Alanine-Proline-Glycine-Valine-Glycine |
| 27 | LGVGG | 401 | Leucine-Glycine-Valine-Glycine-Glycine |
| 28 | VLPG | 384 | Valine-Leucine-Proline-Glycine |
| 29 | FRAAA | 534 | Phenylalanine-Arginine-Alanine-Alanine-Alanine |
| 30 | VGGVPG | 484 | Valine-Glycine-Glycine-Valine-Proline-Glycine |
| 31 | FGPGG | 433 | Phenylalanine-Glycine-Proline-Glycine-Glycine |
| 32 | VGVPG | 427 | Valine-Glycine-Valine-Proline-Glycine |
| 33 | VLPGAG | 512 | Valine-Leucine-Proline-Glycine-Alanine-Glycine |
| 34 | VGLHypG | 458 | Valine-Glycine-Leucine-Hydroxyproline-Glycine |
| 35 | LGVGA | 415 | Leucine-Glycine-Valine-Glycine-Alanine |
| 36 | AFPG | 390 | Alanine-Phenylalanine-Proline-Glycine |
| 37 | AFPGA | 461 | Alanine-Phenylalanine-Proline-Glycine-Alanine |
| 38 | VGIPA | 455 | Valine-Glycine-Isoleucine-Proline-Alanine |
| 39 | VGGIPT | 542 | Valine-Glycine-Glycine-Isoleucine-Proline-Threonine |
| 40 | VGVGVPG | 583 | Valine-Glycine-Valine-Glycine-Valine-Proline Glycine |
| 41 | LGPGVG | 498 | Leucine-Glycine-Proline-Glycine-Valine-Glycine |

*SEQ IDs 23 and 32 appear to be a common sequence because Proline hydroxylation is a post-translational event.

Additional Peptides

Additional peptides were synthesized. A general method for synthesizing peptides is described in U.S. Pat. No. 4,816,513 to Bridgham et al., incorporated herein by reference thereto in its entirety, which describes a process for automatically constructing a polypeptide. Additionally, U.S. Pat. No. 4,668,476 to Bridgham et al., incorporated herein by reference thereto in its entirety, also describes an apparatus for automatically constructing a polypeptide and a transfer system to transfer activated species from the activator system to the reaction vessel and to transfer amino acids, reagents, gases and solvents from one part of the apparatus to another. Generally, this synthesis process is conducted using Fmoc chemistry on automated solid phase synthesizers, (or in some cases by Boc chemistry). The synthesized peptides are generally purified by HPLC using reversed phase C4 and C18 columns. Alternate purification methods include ion exchange and gel filtration chromatography.

Table II illustrates some additional peptides which were synthesized. SEQ IDs 45-48 illustrate various modifications of VVPQ at either the amino terminus or carboxy terminus of the peptide. SEQ IDs 49-51 have been modified to include a cysteine residue at both the carboxy and amino terminus of the peptides. The cysteine residues provide a sulfhydryl group at each end of the chain which permits convenient formation of cyclic disulfide. Finally, SEQ IDs 52-54 are very similar to SEQ IDs 49-51, but they have copper as a cheating agent to form a cyclic structure.

TABLE II

| SEQ # | PEPTIDE | MOL WT | NAME (N-to-C-terminal) |
|---|---|---|---|
| 42 | VVPQNH$_2$ | 448 | Valine-Valine-Proline-Glutamine-Amide |
| 49 | CVVPQC (cyclic) | 647 | Cysteine-Valine-Valine-Proline-Glutamine-Cysteine |

TABLE II-continued

| SEQ # | PEPTIDE | MOL WT | NAME (N-to-C-terminal) |
|---|---|---|---|
| 50 | cyclo(CAVVPQC) | 718 | Cysteine-Alanine-Valine-Valine-Proline-Glutamine-Cysteine |
| 51 | cyclo(CGAVVPQC) | 775 | Cysteine-Glycine-Alanine-Valine-Valine-Proline-Glutamine-Cysteine |
| 52 | cyclo(CVVPQC)–Cu | 64 / 647 | Copper / Cysteine-Valine-Valine-Proline-Glutamine-Cysteine |
| 53 | cyclo(CAVVPQC)–Cu | 64 / 718 | Copper / Cysteine-Alanine-Valine-Valine-Proline-Glutamine-Cysteine |
| 54 | cyclo(CGAVVPQC)–Cu | 64 / 775 | Copper / Cysteine-Glycine-Alanine-Valine-Valine-Proline-Glutamine-Cysteine |

Additionally, SEQ ID 55 was synthesized to replace the glutamine of SEQ ID 17 with an asparagine (Asp-"N") residue, the glutamine residue and asparagine residue having similar charge properties. Modifications were made to SEQ ID 52 that were very similar to those made to SEQ ID 17. These modified or synthetic peptides are illustrated in Table III.

TABLE III

| SEQ # | PEPTIDE | MOL WT | NAME (N-to-C-terminal) |
|---|---|---|---|
| 55 | VVPN | 427 | Valine-Valine-Proline-Asparagine |
| 56 | AVVPN | 498 | Alanine-Valine-Valine-Proline-Asparagine |
| 57 | GAVVPN | 555 | Glycine-Alanine-Valine-Valine-Proline-Asparagine |
| 58 | AVVPNNH₂ | 505 | Alanine-Valine-Valine-Proline-Asparagine-Amide |
| 60 | cyclo(CVVPNC) | 633 | Cysteine-Valine-Valine-Proline-Asparagine-Cysteine |
| 61 | cyclo(CAVVPNC) | 704 | Cysteine-Alanine-Valine-Valine-Proline-Asparagine-Cysteine |
| 62 | cyclo(CGAVVPNC) | 761 | Cysteine-Glycine-Alanine-Valine-Valine-Proline-Asparagine-Cysteine |
| 63 | cyclo(CVVPNC)–Cu | 64 / 663 | Copper / Cysteine-Valine-Valine-Proline-Asparagine-Cysteine |
| 64 | cyclo(CAVVPNC)–Cu | 64 / 704 | Copper / Cysteine-Alanine-Valine-Valine-Proline-Asparagine-Cysteine |
| 65 | cyclo(CGAVVPNC)–Cu | 64 / 761 | Copper / Cysteine-Glycine-Alanine-Valine-Valine-Proline-Asparagine-Cysteine |

SEQ ID 19 was used as a base model for the synthesis of the peptides shown in Table IV below

TABLE IV

| SEQ # | PEPTIDE | MOL WT | NAME (N-to-C-terminal) |
|---|---|---|---|
| 66 | LGAGGAGV | 600 | Leucine-Glycine-Alanine-Glycine-Glycine-Alanine-Glycine-Valine |
| 67 | LGAGGAGVL | 713 | Leucine-Glycine-Alanine-Glycine-Glycine-Alanine-Glycine-Valine-Leucine |
| 68 | LGAGGAGVNH₂ | 607 | Leucine-Glycine-Alanine-Glycine-Glycine-Alanine-Glycine-Valine-Amide |
| 69 | LGAGGAGVLNH₂ | 720 | Leucine-Glycine-Alanine-Glycine-Glycine-Alanine-Glycine-Valine-Leucine-Amide |
| 70 | cyclo(CLGAGGAGC) | 707 | Cysteine-Leucine-Glycine-Alanine-Glycine-Glycine-Alanine-Glycine-Cysteine |
| 71 | cyclo(CLGAGGAGVC) | 806 | Cysteine-Leucine-Glycine-Alanine-Glycine-Glycine-Alanine-Glycine-Valine-Cysteine |
| 72 | cyclo(CLGAGGAGVLC) | 919 | Cysteine-Leucine-Glycine-Alanine-Glycine-Glycine-Alanine-Glycine-Valine-Leucine-Cysteine |
| 73 | cyclo(CLGAGGAGC)–Cu | 64 / 707 | Copper / Cysteine-Leucine-Glycine-Alanine-Glycine-Glycine-Alanine-Glycine-Cysteine |
| 74 | cyclo(CLGAGGAGVC)–Cu | 64 / 806 | Copper / Cysteine-Leucine-Glycine-Alanine-Glycine-Glycine-Alanine-Glycine-Valine-Cysteine |
| 75 | cyclo(CLGAGGAGVLC)–Cu | 64 / 919 | Copper / Cysteine-Leucine-Glycine-Alanine-Glycine-Glycine-Alanine-Glycine-Valine-Leucine-Cysteine |

Pharmaceutical Compositions and Administration

Compositions may be therapeutic, pharmaceutical, cosmetic and the like. Compositions containing the peptides may be generally formulated at an effective concentration within the therapeutic, pharmaceutical or cosmetic composition. The therapeutically effective concentration may be in a range of about 0.0002% to about 90% by weight of the peptide or peptide-like compound. In one example, the peptide concentration is between about 0.5% to about 10% of the composition.

The compositions may be formulated for delivery by a variety of routes. Delivery may be topical, to the skin for example. Delivery may also be by subcutaneous, intravenous (IV), transcutaneous, intramuscular, oral, nasal, aerosol, patch and others. The compositions may be formulated for other applications. For example, compositions may also be formulated for use to coat surgical devices such as stents and the like.

The composition may be formulated as a cosmetic preparation to be applied topically to a patient's skin, such as in an emulsion (e.g., water and oil type, oil and water type), lotion, spray, powder, ointment, cream, foam, aerosol, cream (e.g., face or body), sun lotion, after-sun lotion or other topical administration vehicle. U.S. Pat. No. 4,327,078 to Charlet et al. is illustrative of the different types of topical administrations which may be employed.

Compositions may be in the form of a peptide or peptides in combination with at least one other agent, such as stabilizing compound, which may be administered in any sterile, bio-compatible pharmaceutical carrier, including, but not limited to saline, buffered saline, dextrose, and water. The compositions may include salts, buffering agents, preservatives, adjuvants, other vehicles and the like.

The example compositions may be used in many different galenic forms for their percutaneous administration. Example forms may include forms suitable for cosmetics and which permit production of creams, pastes, gels, lotions, "water-in-oil" and "oil-in-water" emulsions as well as forms composed of liposomes, simple or mixed micelles, or other penetration promoters such as lysophospholipids, cyclodextrins, polyethylene glycol, surface active agents, alcohols, fatty acids and vegetable oils. This list may not be limitative and other presentations known to man can be envisaged. Generally, the compositions may have the property of being hydrosoluble and/or liposoluble. Hence, cosmetic and dermatological compositions may be in the form of creams, lotions, gels and ointments (e.g., topical preparations) or any other form generally used for topical applications. In addition, the compositions may be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. U.S. Pat. No. 4,327,078, incorporated herein as if set forth in its entirety, is illustrative of the different types of topical administrations which may be employed to administer the composition of the present invention.

The compositions may be administered to a patient alone, or in combination with other agents, drugs, hormones, steroids, retinoids, skin enhancing agents and the like. Pharmaceutically-acceptable carriers may also include excipients and auxiliaries which facilitate processing of the active compounds into preparations which can be used pharmaceutically. Further details on techniques for formulation and administration may be found in Remington's Pharmaceutical Sciences. The pharmaceutical composition may be provided as a salt and can be formed with many acids, including but not limited to, hydrochloric, sulfuric, acetic, lactic, tartaric, malic, succinic, etc. Salts may be more soluble in aqueous or other protonic solvents than are the corresponding free base forms. After pharmaceutical compositions have been prepared, they can be placed in an appropriate container and labeled for treatment of an indicated condition. Such labeling may include amount, frequency, and method of administration.

7-Hydroxylated Steroids

The peptide compositions including peptides may include, for example, 7-hydroxylated steroids. Such compositions may be useful for preventing and/or treating the effects of aging and of the action of ultraviolet (UV) light, for example. Example 7-hydroxylated steroids may include derivatives of pregnenolone (PREG) and dehydroepiandrosterone (DHEA). Some 7-hydroxylated steroids include, for example, 7α-hydroxy-DHEA in circulation in pre-menopausal women have been measured at 200-300 pg/ml, 30-7α-dihydroxy-5α-androstan-17-one (7α-hydroxy-isoandrosterone). Other steroids that may be hydroxylated at the 7 position may include, for example, PREG, 5 α-androstane-3,β, 17β-diol, 3β-hydroxy-5α-androstan-17-one and 3β-hydroxy-5α-pregnan-20-one. Some 7-hydroxylated derivatives of DHEA may be found in tissues of the human fetus, in the amniotic epithelium, the human liver, the testicles and human epididymus and in human pre-adipocytes, for example. In one example, the 7-hydroxylated derivatives of steroid compounds may be obtained from a Fusarium moniliforme system In one example, a peptide composition may include 7α or 7β substituted compounds of DHEA or PREG. The compounds may or may not be reduced at position 5. The formulas for these example compounds are illustrated in the example formulas shown in (I) and (II) below.

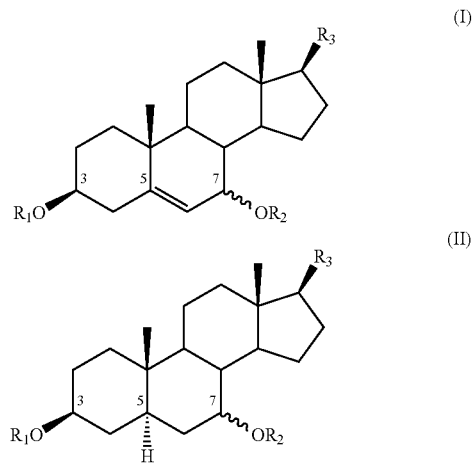

In these illustrated example formulas:

$R_1$ may include, for example: a hydrogen atom, functional groups which are an ester of an organic acid with 1 to 24 carbon atoms, a sulfate ester or a phosphate ester, or a carbonaceous ether with 1 to 24 atoms of carbon that includes zero or several nitrogen atoms, carbohydrate ethers with 3 to 100 carbon atoms and their derivatives that contain or do not contain, and one or several atoms of nitrogen.

$R_2$ may include, for example: a hydrogen atom or a functional group that is an ester of a fatty acid with 1 to 24 carbon atoms.

$R_3$ may include, for example: a hydrogen atom, an —OH group, groups of the formulas: —CO—$R_4$, —CHOH—$R_4$, =CH—$CH_3$, =COH—$CH_3$, —$CHR_4$—$CH_3$, =O, in which $R_4$ is a substituted or non-substituted alkyl group containing from 1 to 10 carbon atoms, that may be a methyl group.

Example compounds which may be included in this invention are the 7α or 7β substituted derivatives of DHEA or PREG. These example compounds may be and more particularly 7α or 7β hydroxylated derivatives, reduced or not reduced in position 5.

One group of example compounds are 7α hydroxylated derivatives in which the oxygen in the 7 position is axial (7α) and the $R_2$ substituent is hydrogen. Another group of example compounds are those where $R_1$ is hydrogen. Specific example of these compounds is 7α-hydroxy-DHEA and 7α-hydroxy-isoandrosterone where $R_3$ is a ketone (=O).

Derivatives of the example compounds in which $R_1$ is an organic acid may have enhanced liposolubility. This property may provide improved retention of the compounds in the cells, at the membranes for example, and may provide lengthened effects on cells. Examples of these compounds may be those in which $R_1$ is a palmitate, an oleate or a ferulate. In one example, the compounds may be 3β-palmitoyl-DHEA, 3β-pleyl-DHEA or 3β-feruloyl-DHEA.

The example cosmetic and/or dermatological compositions may include one or several steroid derivatives as well as other compounds such as those known for their cosmetic or dermatological property. Examples of such compounds may include hormones, and/or the additives or vehicles traditionally used in these fields.

In one example, the use of a steroid derivative in a cosmetic composition intended to compensate for, treat and/or prevent the cutaneous effects of aging and/or the effects of UV irradiation on the skin, may be administered at a dose of between 0.05 and 10 mg per application and per day. Another example administration may be between 0.05 and 5 mg per application and per day.

Retinoids

The peptide compositions including peptides may include, for example, retinoids (e.g., Vitamin A and its derivatives). A variety of example retinoids may be used. Some example retinoids include retinoic acid, retinol (Vitamin A alcohol) and tretinoin. Other retinoids may be used.

Tretinoin, for example, is (all E)-3,7 dimethyl-9-(2, 6,6-trimethyl-1-cyclohexen-1-yl)-2,4,6,8-nonatetraenoic acid. Tretinoin is also referred to as all-trans-retinoic acid. Retin A and RENOVA® are brands of tretinoin (a short for trans-retinoic acid), a substance related to but distinct from vitamin A. RENOVA® differs from Retin A in that it contains a moisturizing cream. Retin A (RENOVA®) may produce multiple effects in the skin, including increasing the responsiveness of skin cells to epidermal growth factor (EGF).

In one example, a typical strength of topical tretinoin (Retin A, RENOVA® creams is 0.0250-0.1 percent. In one example, 0.025 percent Retin A may be as effective as 0.05 or 0.1 percent, but with lower incidence of skin irritation. For people with sensitive skin, 0.025% Retin A (RENOVA®) may be the optimal strength. Improvement on tretinoin (Retin A, RENOVA® may continue for up to a year of continued use.

Additional Substances for Use with Peptides

A variety of other substances may be used with compositions containing the peptides. These substances may be called "skin enhancing agents." In one example, Vitamin C (ascorbic acid) and/or its derivatives may be used as a skin enhancing agent. In another example, salicylic acid and/or products containing salicylic acid may be used as a skin enhancing agent.

Conditions for which the Peptides may be Beneficial

The peptide or peptides described herein, as well as their corresponding therapeutic compositions may have a variety of applications. The following descriptions provide a summary of some of the conditions these peptide(s) may likely benefit.

Skin conditions: There are many skin conditions and diseases which may benefit from elastin peptide treatment. One use is in cosmetic applications (i.e., to provide increased tone, turgor, and appearance). For example, the inherited disease scleroderma is characterized by a thickening and stiffening of the skin, and cutaneous ulcers due to the overproduction of collagen (there are a number of diseases which involve overproduction of collagen and which seem to have an adverse effect on elastin production/content and compromise the tissue). This disease can also have systemic effects on organs and blood vessels. The stiffness and difficulty in motion along with the cutaneous ulcers may benefit greatly from incorporation of elastin into the skin. A similarly positive outcome may occur with the treatment of lupus and rheumatoid related skin changes which are generally collagen-vascular diseases involving a decrease in elastin.

Other skin conditions may benefit from the peptides. Conditions and problems such as acne rosacea, acne vulgaris, aging skin with vascular fragility, burn treatment, scar contractures from burns, radiation burns, purities (or chronic itching), psoriasis, urticaria (commonly referred to as hives), xerosis (abnormal dryness of the skin, eyes or mouth), vesicular dermatoses, cracked fingers and feet, drug eruptions (from an allergic reaction), epidermolysis (a skin condition where the epidermis is in a loosened state, often with the formation of blebs and bullae either spontaneously or after trauma), and erythema multiforme may benefit from treatment with the elastin peptide(s) described herein.

Additionally, there are heritable skin disorders such as cutis laxa and EDS or Ehlers Danlos Syndrome (a group of connective tissue disorders in which the skin hangs in loose pendulous folds believed to be caused by decreased elastic tissue formation as well as an abnormality in elastin formation or an excess of collagen), EDS, elastoderma, progeria, and pseudoxanthoma elasticum (an inherited disorder in which elastic fibers found in many tissues slowly become calcified) which may benefit from an increase in elastin in the affected tissues.

It is believed that the application of the elastin peptides of the present invention would result in an increase in tissue elastin and may provide effective treatment for serious diseases such as pemphigus.

Tendons, Sheaths and Bone: Tendons, sheaths and bone are comprised in part of elastin. Chronic, painful conditions affecting some of these tissues include carpal tunnel disease, fasciitis, flat feet, and tendonitis. These conditions and similar ones may be improved with increased levels of elastin in the affected tissue. Bone spurs, fascial tears, ligament tears and tendon tears may heal faster with supplemental elastin provided by the elastin peptides of the present invention. These tissues may become stronger as a result of stimulation of elastin production accompanying this treatment. Additionally, cartilage growth abnormalities may be corrected by application of elastin peptides.

Treatment with the elastin peptides may also be useful in veterinary medicine for skin ulcerations in livestock such as horses and cattle. Hoof problems can be very painful and problematic for horses and other hoofed animals. Hoof conditions may benefit from increased elastin levels which could be provided and induced by treatment with elastin peptides.

Hair: Hair growth, color, and removal may all be improved by treatment with elastin peptides which may make the hair stronger, more shiny, and improve the condition and healing of irritated skin upon removal of unwanted hair. Premature graying of hair may also be due to decreased elastin.

Lips: Chapped lips and chronic dermatitis or inflammation of the lips may be greatly improved upon treatment with elastin peptide. Long-term relief may be a potential benefit from the stimulation of endogenous elastin in these tissues.

Back: The breakdown of elastin in the spine may contribute to herniated disks and lead to acute and/or chronic pain. Replacing elastin with peptides of the present invention along with the stimulation of endogenous elastin may result in improved healing of the disk and reduce or eliminate the pain associated with this condition, especially when combined with other treatments, such as steroids.

Brain and nervous system: In nerve compression syndromes, treatment with elastin peptides of the present invention may stimulate endogenous elastin production in certain neurological conditions and/or promote revascularization after stroke and neural tissue transplants. This revascularization may greatly improve the clinical outcome of these treatments.

Autoimmune diseases: Lupus and other rheumatoid related diseases are characterized by localized destruction or degeneration of elastin in tissues throughout the body. These and similar diseases may greatly benefit from treatment with elastin peptides of the present invention which may promote restoration of damaged tissue and provide long-term benefit from the stimulation of endogenous elastin.

Lungs: Many lung diseases including chronic obstructive pulmonary disease, laryngeal stenosis, pulmonary fibrosis, pulmonary sarcoid and tracheal stenosis are associated with a decrease in elastin, a component for maintaining the elasticity and proper functioning of the lung. Often, these lung conditions are due to a decrease in particular proteases which normally balance the activity of elastin-degrading proteases, referred to generally as elastases. An example of this type of deficiency is alpha 1 protease inhibitor deficiency. A decrease in elastin due to this type of deficiency causes a breakdown of the lung matrix which is vital for proper lung function. Other factors, such as smoking can also lead to breakdown of the elastin component of the lung matrix.

Muscle: Muscles are often covered with a thin layer of connective tissue which is comprised of elastin and other components such as collagen. Thus, applying peptides of the present invention to muscle tissue may increase muscle tone and the healing of muscle tears, and generally strengthen muscles by increasing their elastin content.

Joints: Similarly, joints are comprised of connective tissue, including elastin. In many cases, individuals suffer from joint pain and joint abnormalities as a result of inflammatory disease or from wear and tear which all generally result in decreased amounts of elastin present in the connective tissue of joints. Thus, many joint diseases or problems such as athletic joint injuries, torn cartilage and/or ligaments, osteoarthritis, joint pain, rheumatoid arthritis, and stiff joints may benefit from treatment with elastin-peptides of the present invention. These elastin peptides may have the capability to stimulate endogenous elastin in these tissues and may provide substantial and long-term rebuilding and maintenance of the elastin in these tissues.

Nails: Elastin is useful in treating and preventing nail brittleness, split nails, and to enhance the hardness of nails in general. Nails are comprised of flattened epidermal cells and have a high concentration of elastin in the nail bed. Thus, increasing the elastin content of these cells may result in a stronger and more flexible nail.

Blood vessels/lymphatics: Elastin is an important constituent of vessels. Application of elastin to affected tissues in vascular diseases which involve abnormalities of arteries or veins including atherosclerotic occlusive disease, chronic venous insufficiency, diabetic vasculitis (inflammation of a vessel caused by diabetes), fibrotic mediastinitis associated with superior vena cava syndrome (an exuberant inflammatory sclerogenic process of infectious, rheumatic, hemorrhagic, or undetermined origin, often accompanied by obstruction of mediastinal structure, especially the vena cava), varicose veins, temporal arteritis, stasis dermatitis, and lymphedema (including elephantiasis, which is a chronic unilateral or bilateral edema of the extremities due to accumulation of interstitial fluid as a result of the stasis of lymph, which is caused by an obstruction of the lymph vessels).

Breast: Capsule contractures secondary to breast implants are disorders of fibers and are conditions of fixed high resistance (rigidity) to passive stretch of a muscle. Fibrocystic disease, selected cases of breast cancer where there is tissue loss may benefit from treatment with elastin peptides.

Cartilage growth: Transformation of hyaline cartilage to elastin cartilage in remaking of structures such as an ear, nose, larynx or any structure in which elastic cartilage would be beneficial, may be aided by treatment with elastin peptides.

Ear: Chronic serous otitis media and hearing loss secondary to otitis media as well as other diseases causing scarring of the ear drum may benefit from replacement of elastin which can serve to repair scarred ear drum tissue caused by these chronic infections.

Eye: Eye disorders such as diabetic retinitis, retinal hemorrhages associated with pseudoxanthoma elasticum (PXE), macular degeneration, and retinitis pigmentosa all involve abnormalities of the retina which is comprised in part of elastic fibers. PXE is an inherited disorder in which elastic fibers become slowly calcified, producing characteristic changes in the skin, the retina of the eye, and the cardiovascular system. Incorporation of healthy, normal elastin peptides to the retinas of individuals affected by these disorders may improve vision and lead to healing of the retina and prevention of further damage caused by the lack of or presence of malformed elastin is this tissue.

Genito-urinary tract: There are various genito-urinary conditions which are associated with either chronic inflammation or other condition leading to a decrease in elasticity of connective tissue, or with the narrowing of canals or ducts (strictures). The replenishing of elastin or the reversal of the strictures by treatment with elastin and the stimulation of endogenous elastin may benefit a number of genito-urinary conditions including benign prostatic hyperplasia, chronic sclerosing vaginitis, glomerular sclerosis, ureteral stricture, urethral stricture and use with urethral stents, uterine benign fibroids, and vaginal stenosis.

Gastrointestinal tract: A number of GI conditions are the result of chronic inflammation, or abnormal thickening or calcification of GI tissues including anal fissures, chronic pancreatitis, esophageal stenosis, esophageal varicies, hemorrhoids, intestinal adhesions, and pyloric stenosis. Crohn's disease, as well as other localized inflammatory/fibrotic bowel diseases, are characterized by a chronic granulomatous inflammatory condition of unknown etiology. Scarring and thickening of the bowel wall frequently leads to intestinal obstruction and the formation of fistula and abscesses. Supplying elastin to these tissues may improve gastrointestinal function in these patients and restore the normal balance of connective tissue components in the gastrointestinal tract. Similarly, in biliary cirrhosis and fibrotic liver diseases such as liver cirrhosis, diffuse and interlacing bands of fibrous tissue form and replace the normal liver lobules.

Immunology: Enhancement of the immune response through cytokine activation as well as suppression of immunity for prevention of transplant rejection and for treatment of autoimmune disorders may be mediated by altering elastin levels. Human activated lymphocytes express the elastin-laminin receptor. The expression of the elastin-laminin receptor is a general property of most activated human lymphocytes, but is dependent upon lymphocyte subsets. Elastin peptides activate these receptors and trigger the stimulation of biosynthesis and release of an elastase.

Ulcerations: Ulcers are defects or excavations of the surface of an organ or tissue, produced by the sloughing of inflammatory tissue. Common ulcerative disorders include esophageal, duodenal, and gastric ulcers. It is believed that providing ulcerative tissues with elastin may speed the healing of the affected tissue and possibly even strengthen the tissue by stimulating endogenous elastin production.

Blood Vessels/Heart: Since large amounts of elastin are found in the walls of blood vessels, particularly in the arch of the aorta near the heart, it is important to maintain the normal healthy balance of elastin in blood vessels and other vessels (such as lymph vessels). Additionally, in pulmonary tissues, the subendothelium is comprised of the internal elastic lamina, a layer which normally separates the endothelium from the underlying smooth muscle cells. In many cardiac diseases, such as congestive heart failure, coronary artery disease, homocystinuria, restrictive pericarditis, sclerosing endocarditis, supra ventricular aortic stenosis, this internal elastic lamina is compromised due to the breakdown of elastin resulting in a remodeling of this matrix layer. This breakdown is often the result of an imbalance in enzyme(s) (such as elastase) which degrade elastin. In some cases, such as in Marfan's syndrome, the elastin malformations are due to an autosomal dominant, congenital disorder affecting connective tissue. Thus, providing affected tissue with normal elastin peptides may be a useful treatment for strengthening the connective tissue in individuals with Marfan's syndrome.

A bacterial infection caused by the group A beta hemolytic Streptococci resulting in rheumatic fever can sometimes lead to rheumatic heart disease, a serious condition characterized by inflammation, and degeneration of connective, tissue structures of the body, especially of the heart valves. Treatment of tissues affected by rheumatic heart disease with elastin peptides may allow these tissues to heal and be rebuilt. Additional clinical uses of supplemental elastin peptides include as arterial stents to enhance internal elastic membrane regeneration in angioplasty procedures.

Hypertension: High arterial blood pressure (generally hypertension) can be the result of multiple and diverse etiologies including congenital heart defects, chronic lung disease, hepatic disorders, and autoimmune disease (particularly scleroderma). Hypertension is often marked by endothelial perturbations as well as abnormalities in the subendothelium. These subendothelial problems are manifested in the breakdown of the internal elastic lamina, often by an enzyme which degrades elastin. This breakdown results in the remodeling or rearrangement of the laminar matrix which may result in chronic hypertension. Correcting the elastin composition of the internal elastic lamina with supplemental elastin peptides would improve this condition and would likely augment the standard treatment which includes elastase inhibiting drugs.

With blood vessel and hypertension, a suitable use of the peptides of the present invention may be along with a stent. Depending on the nature of the stent, the stent may have the therapeutic mixture (e.g., peptide(s) alone or in combination with other therapeutic uses) incorporated in the body of the stent or coated thereon. For incorporation, normally a biodegradable plastic stent may be used which will release the therapeutic agents while supporting the vessel and protecting against restenosis. In the fabrication of the stent, the biodegradable matrix may be formed by any convenient means known in the art. Alternatively, the stent may be coated with the therapeutic mixture, using an adhesive or coating which allows for controlled release of the therapeutic mixture. The stent may be dipped, sprayed or otherwise coated with a composition containing the NO precursor agent or the therapeutic mixture and a matrix, such as biodegradable polymers, a physiologically acceptable adhesive, proteins, polysaccharides or the like. By appropriate choice of the material for the stent and/or the coating comprising the therapeutic mixture, a physiologically active amount of the therapeutic mixture may be maintained at the site of the vascular injury, usually at least one day and up to a week or more.

EXAMPLES

The following examples are provided to better illustrate the subject matter herein. The examples are not meant to limit the scope of the claimed subject matter.

Example 1

Preparation of Elastin Peptides by Digestion

A ligament extraction process was used. *Ligamentum nuchae* ligaments were dissected and as much fat and excess connective tissue as possible was removed. These "clean" ligaments were then chopped into about one centimeter square (1 cm$^2$) pieces and washed with doubly distilled water ("DDW"). The clean ligaments were then placed on a metal mortar, pre-chilled to −20° F. and liquid nitrogen is added to freeze the tissue. The ligaments were then minced or pulverized and re-suspended in 1% aqueous NaCl at a ratio of about 100 grams of tissue to about three liters of 1% aqueous NaCl and homogenized in a Waring blender at high speed for 30-60 seconds. The homogenized ligament was transferred to a four-liter beaker and stirred overnight at 4° C. on a magnetic stirrer, after which it was centrifuged at 32,500×G and the supernatant is checked for protein content using the Biuret method for protein determination.

The Biuret reaction was performed by mixing 2 milliliters of extract with 3 milliliters of reagent and reading immediately either by simple visual inspection or at 540 nanometers on a spectrophotometer to determine the protein concentration of the supernatant. The supernatant was then discarded. The pellet (i.e., the elastin pellet) was resuspended in 1% aqueous NaCl and homogenized. The process of homogenizing in a Waring blender, stirring overnight and centrifuging was repeated three to four times until the supernatant was Biuret negative. After centrifugation, the elastin pellet was resuspended in DDW and autoclaved 30 psi for six hours. The resuspended elastin pellet was centrifuged again and the supernatant was tested for protein content via the Biuret method. The elastin was washed with boiling DDW and then with DDW at room temperature and the washes were tested for protein content via the Biuret method. If the washes were Biuret negative, the elastin pellet were dried with chloroform/methanol solution at a ratio of 2 parts chloroform to 1 part methanol. If the Biuret test were positive, the six hour autoclave procedure with wash step was repeated until the Biuret test was negative. Finally, the elastin residue was washed with five volumes of pure methanol and air-dried at room temperature. The elastin residue was transferred to a desiccator and dried over $P_2O_5$ for 24 hours until the weight of the elastin residue was stable. The elastin residue was then milled in a Willey mill through a 40-mesh screen followed by a 60-mesh screen.

Digestion used thermolysin. Three times re-crystallized thermolysin product from CalBiochem (10394 Pacific Center Court, San Diego, Calif. 92121) was used. The thermolysin preparation contained sufficient calcium to ensure maximal activity of the enzyme. The thermolysin digestion was done as follows: a water bath was brought to 55° C. with a rotary shaker and five grams of the finely milled largely insoluble elastin residue was hydrated with one liter of DDW for fifteen minutes at room temperature. After hydration, the one liter of DDW which contained the five grams of elastin was placed in the 55° C. bath and the pH of the elastin/water mixture was brought to a pH between 7-8 with 10% methylamine. Fifty milligrams of thermolysin (from *Bacillus thermoproteolyticus*) was added directly to the elastin water mixture. The thermolysin contained about 60% protein (60.2%), about 13% (13.2%) sodium acetate, and about 25% (25.3%) calcium acetate, with a specific activity of about 8,720 I.U./mg dry weight. The pH of the elastin water mixture was monitored with a pH meter or pH stat and adjusted with 10% methylamine to keep the pH between 6.8 and 7.5. The digestion was allowed to continue for 75 minutes and then concentrated hydrochloric acid was added to adjust the pH to 3.0 to terminate the digestion.

After digestion was terminated, the digested product was filtered through a PM 10 Diaflow 10,000 molecular weight cutoff ultra-filtration membrane to filter out any protein or peptides exceeding about 10,000 Da molecular weight. The resulting supernatant was a composition comprised of peptides having a molecular weight of less than about 10,000 Da.

The elastin peptide fragment/water mixture was flash evaporated to dryness and re-dissolved in a small volume of DDW. Alternatively, the mixture was diluted sufficiently with DDW for lyophilization to dryness. In the alternative, rather than re-dissolving the elastin peptide(s), the filtered product was freeze dried twice, resulting in a powder Example 2

Increased Elastin Production from Application of Peptides to Mammalian Skin

Topical treatment of Sprague-Dawley male rats with a composition including peptides (i.e., SEQ IDs 1-41) at a concentration of about 1.3% (wt/wt) of the formulation over a one month period was performed. The rats were treated topically with a 1.3% concentration (wt/wt) of the preparation of the hydrophilic elastin peptide for a period of 30 days. FIG. 1 shows the results for S CONTR (shaven control), US CONTR (unshaven control), DHEA (dehydroepiandrosterone) and HEP (composition including peptides). Three animals each were used to generate the data for S CONTR, US CONT, and DHEA and eleven animals were used for HEP. Three skin samples from the treated areas of each animal were taken for study, and the three results from each animal were averaged. The mean of these results were: S CONTR (1.408); US CONTR (2.291); DHEA (1.753); HEP (3.175). The elastin content of the skin was determined by a precise assay for rat elastin developed by Sandberg, et al. (Connective Tissue Research 25:139-48, 1990) the assay portion of which is hereby incorporated herein by reference thereto. Topical treatment of Sprague-Dawley male rats with a composition including peptides (i.e., SEQ IDs 1-41) at a concentration of about 1.3% (wt/wt) of the formulation over a one month period was performed. The rats were treated topically with a 1.3% concentration (wt/wt) of the preparation of the hydrophilic elastin peptide for a period of 30 days. FIG. 1 shows the results for S CONTR (shaven control), US CONTR (unshaven control), DHEA (dehydroepiandrosterone) and HEP (composition including peptides). Three animals each were used to generate the data for S CONTR, US CONT, and DHEA and eleven animals were used for HEP. Three skin samples from the treated areas of each animal were taken for study, and the three results from each animal were averaged. The mean of these results were: S CONTR (1.408); US CONTR (2.291); DHEA (1.753); HEP (3.175). The elastin content of the skin was determined by a precise assay for rat elastin developed by Sandberg, et al. (Connective Tissue Research 25:139-48, 1990) the assay portion of which is hereby incorporated herein by reference thereto.

The data show that the endogenous elastin (measured by microgram (μg) Elastin per milligram (mg) Skin Fat Free Dry weight) of each of the rats to which the composition was applied doubled over that of a control sample and to a sample which was treated with a 5% concentration of DHEA over a similar time period (FIG. 1). An alpha level less than 0.001 for the data as determined by analysis of variance is significant because there is less than one chance in a thousand that the findings occur by chance.

The data support the use of the cosmetic or pharmaceutical preparation over an extended period, for example in the range of one week to one month at about 1.5% concentration (wt/wt) of elastin peptide or peptides in the pharmaceutical preparation. The data indicates that the peptide containing compositions may enhance the softness or elasticity of the skin. The peptides and formulations may also improve the texture of skin, specifically the physical appearance of the skin.

Example 3

Increased Vasculature in Skin Treated with Peptides

Figure 2B:
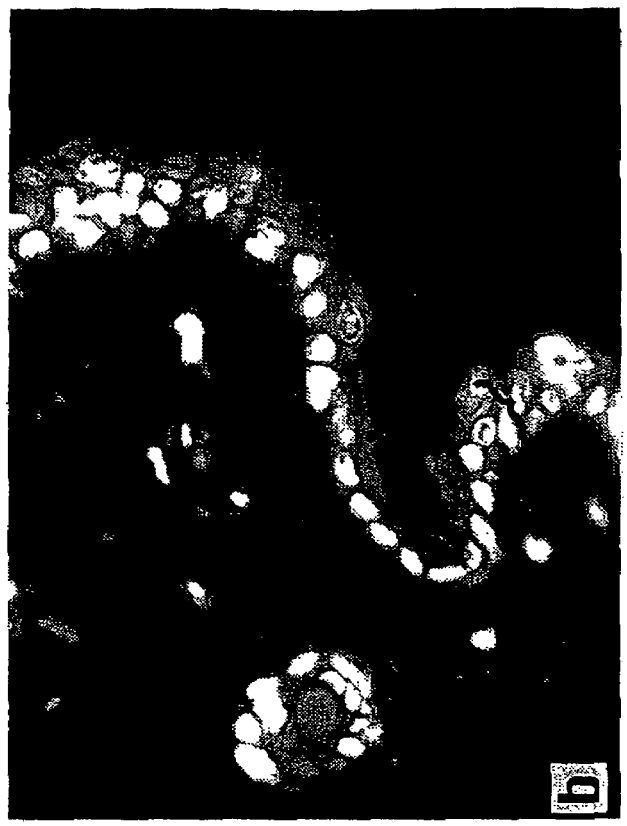
FIG. 2A-D is an example micrograph illustrating the microvascular response of the skin tissue to peptides.
Figure 2A:
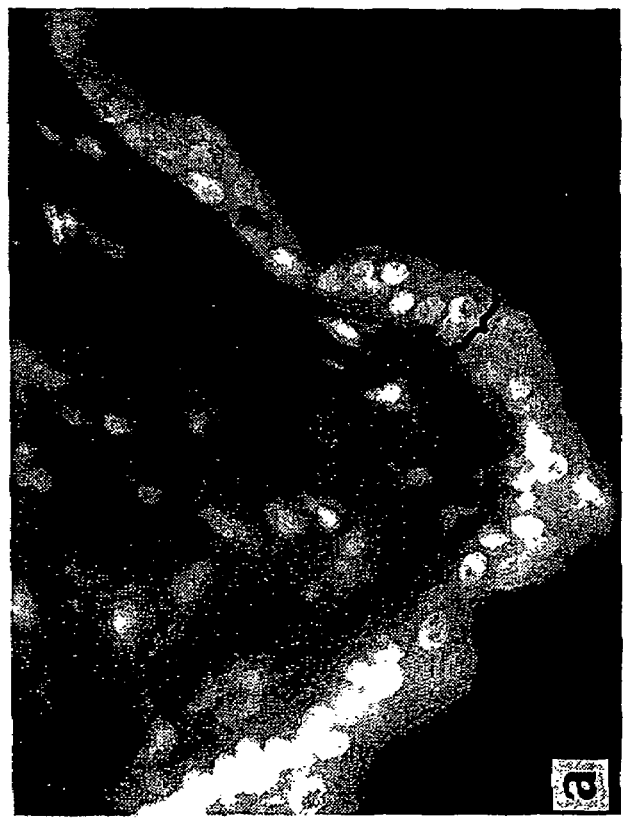
Figure 2D:
Figure 2C:
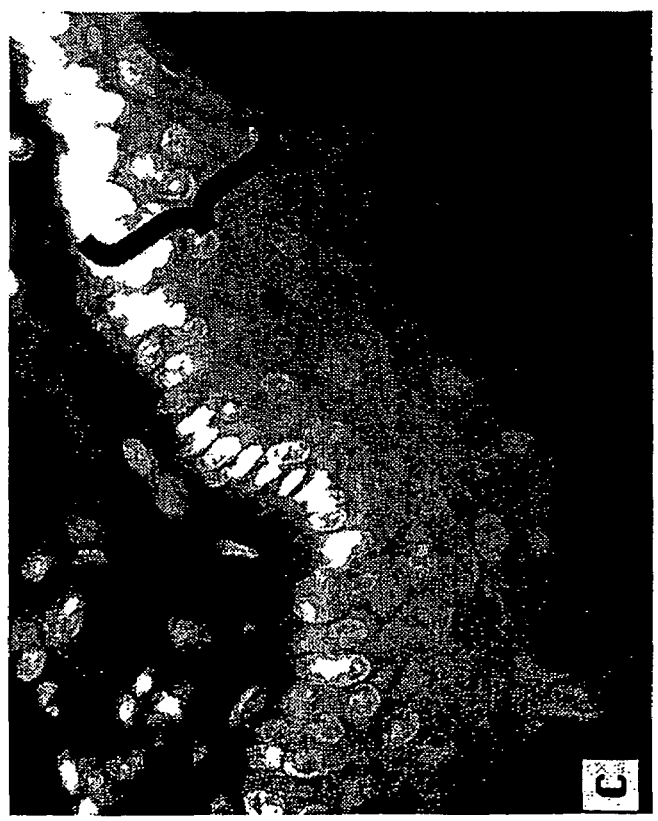

FIGS. 2A-D are fluorescent micrographs of fixed skin cross-sections taken from rats treated as described in Example 3, and stained with fluorescein-conjugated anti-fibronectin antibodies. FIG. 2A is a representative sample from the unshaven control tissue; FIG. 2B is a representative sample from the shaven control sample; FIG. 2C is a representative sample of tissue which received DHEA topical treatment; and FIG. 2D is a representative sample of tissue which received treatment of a composition containing peptides, as described in Example 2. In each of the panels, the dermal layer of the skin is indicated by a bracket. The dermal layers of skin in FIGS. 2A and B are relatively uniform and thin compared to the thickness of the dermal layers in FIGS. 2C and D.

The data show that, compared to FIGS. 2A-C, FIG. 2D (i.e., peptide treated) has increased concentrations of capillary venules in the subdermal region of the skin, based on fluorescent staining. The capillary venules are shown in this figure as brightly stained oval bodies that lie beneath the dermal layer. The increase in the concentration of endothelial cells in the subdermal region indicates an increase in capillary density and therefore illustrates the potential for the peptides and formulations of the present invention to be used for the formation of blood vessels or capillary venules (neovascularization or angiogenesis). These results indicate that the skin treated with the peptide composition may be healthier than untreated skin.

Example 4

Activity of Fractionated Peptides

A study was performed to determine whether different peptides had different activities in promoting skin health. Elastin protein was partially digested with thermolysin and the resulting peptides (i.e., SEQ ID 1-SEQ ID 41) were applied to an HPLC column. Five fractions containing clusters of peptides were collected from the column in the 5-50 minute range. The fractions were tested for activity using a bromodeoxyuridine Triphosphate (BrdUTP) incorporation assay in RFL-6 cells. The assay measures production of mRNA involved in protein synthesis. Table V below shows measurement of increased mRNA in the cells in response to the elastin.

TABLE V

| Fraction # | Approximate Elution time | Approximate % Change w/Control Subtracted Out |
|---|---|---|
| 1 | 5.3 min-11.8 min | 1% |
| 2 | 11.8 min-23.0 min | 4% |
| 3 | 23.0 min-44.1 min | 41% |
| 4 | 44.1 min-45.8 min | 10% |
| 5 | 45.8 min-50.0 min | 2% |
| UNF | Un-fractionalized mixture (SEQ IDs 1-41) | 52% |

The data show that each of the fractions cause an increase in mRNA in RFL-6 cells as compared to backround. The data show that Fraction #3 either alone and/or in combination with other fractions (e.g., as seen with the un-fractioned mixture)

has a greater green fluorescence activity than other of the fractions. Fraction #3 includes SEQ IDs 14-31.

Fraction #3 was sub-fractionated into 10 fractions corresponding to ten major peaks identified on the HPLC (at 215 nm). Table VI below illustrates the green fluorescence intensity as a measure of increased mRNA in RFL-6 cells in response to sub-fractionated portions of Fraction #3.

TABLE VI

| Fractionated # | Seq. No. Contained Therein | Abbreviated Peptide Sequence | % Change of Green Fluorescence Intensity |
|---|---|---|---|
| 1 | SEQ ID 14 | VGPA | 39 |
| 2 | SEQ IDs 15, 16 | VVPG, AVPG | 40 |
| 3 | SEQ ID 17 | VVPQ | 85 |
| 4 | SEQ IDs 18, 19 | VAARPG, LGAGGAG | 44 |
| 5 | SEQ IDs 20, 21 | AIPG, LGPGG | 42 |
| 6 | SEQ ID 22 | AAAQA | 20 |
| 7 | SEQ ID 23 | VGVHypG | 57 |
| 8 | SEQ ID 24 | VYPGG | 38 |
| 9 | SEQ IDs 25, 26, 27, 28, 29 | IGGVGG, VAPGVG, LGVGG, VLPG, FRAAA | 10 |
| 10 | SEQ IDs 30, 31 | VGGVPG, FGPGG | 23 |
| Blank (Background) | | | 30 |

The data suggest that SEQ ID 17 (VVPQ) has the greatest green fluorescence activity, followed by SEQ ID 23 (VGVHypG) and SEQ IDs 18 (VAARPG) and 19 (LGAGGAG).

Example 5

Activity of Synthetic Peptides

Figure 3:
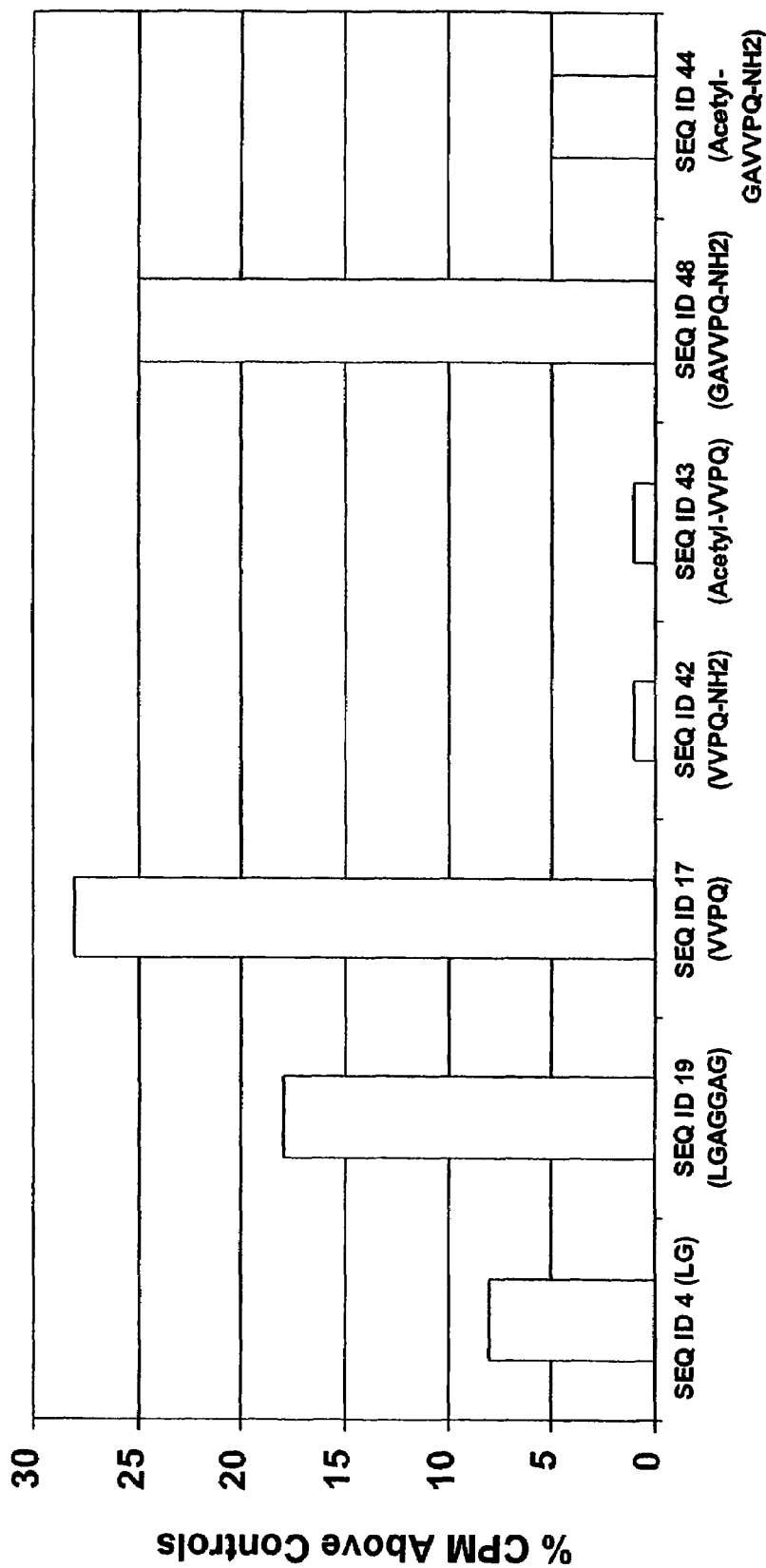
FIG. 3 illustrates the results of an example experiment in a bar graph, showing tritiated thymidine incorporation using selected peptides or peptide-like compounds.

Synthetic peptides were tested for their ability to stimulate incorporation of tritiated thymidine with a 24 hour incubation with RFL-6 cells. Stimulation of incorporation of tritiated thymidine generally is a measure of DNA synthesis which may relate to increased cell division and cell proliferation. The data are shown in FIG. 3. The data indicate that SEQ ID 4 (LG) resulted in about an 8% CPM above the control; SEQ ID 19 (LGAGGAG) resulted in about an 18% CPM above the control; SEQ ID 17 (VVPQ) resulted in about a 28% CPM above the control; SEQ ID 42 (VVPQ-NH$_2$) resulted in about a 1% CPM above the control; SEQ ID 43 (Acetyl-VVPQ) resulted in about a 1% CPM above the control; SEQ ID 48 (GAVVPQ--NH$_2$) resulted in about a 25% CPM above the control; and SEQ ID 44 (Acetyl-GAVVPQ--NH$_2$) resulted in about a 5% CPM above the control. Comparison of the data shown in Table VI with that in FIG. 3 indicates that SEQ ID 17 may be most active in both studies.

While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. For example, the compounds can be administered via many alternative drug delivery vehicles known in the art and the peptides can be derived from digestion of elastin or by amino acid sequencing (either solid state or liquid), as well as from over-expression in a bacterial system. Modification (either chemical or enzymatic) of the basic sequences described herein are also within the purview of the present invention. For example, it appears that a reoccurring pattern in the elastin sequence is the presence of a glycine-alanine residue. Therefore the disclosed sequences may be modified to include this residue at either the amino or carboxyl ends of the peptides. The sequences may also be chemically modified to increase their activity (e.g., amidation of the carboxyl terminus portion of a sequence). The peptides may be chemically modified to increase their activity (e.g., amidation of the carboxy terminus portion of a sequence or including a glycine or alanine residue at either end). Accordingly, all such variances should be viewed as being within the scope of the present invention as set forth in the claims.

The above description has referred to the preferred embodiments and selected alternate embodiments. Modifications and alterations will become apparent to persons skilled in the art upon reading and understanding the preceding detailed description. It is intended that the embodiments described herein be construed as including all such alterations and modifications insofar as they come within the scope of the appended claims or the equivalence thereof.

Example 6

Treatment of Rat Skin with 7-Hydroxy DHEA and 7-Hydroxy Isoandrosterone

Rat skin was treated with 7-hydroxy DHEA and 7-hydroxy isoandrosterone. Skin cross sections were stained with hematoxylin and eosin (H&E) and examined histologically. It was observed that the dermal layer of skin was thickened to nearly twice that of the untreated controls (both shaven and unshaven). There was no change in the outer (keratin) layer nor increase of vascularity of the inner layer of the treated skin sections. The DHEA and derivatives induction of dermal thickening was reversible. A subset of experimental animals within each treatment group were left untreated for 30 days. Upon examination, treated skin sections were indistinguishable from the untreated. Concomitant toxicological studies found no significant toxicity when the compounds were used at 0.5% concentration in a suitable carrier applied twice daily (12 hour intervals) for 30 days.

Example 7

Scavenging of Free Radicals

The ability of a compound to scavenge free radicals may implicate it as an anti-oxidizing agent. To test whether DHEA or it derivatives had the ability to capture free radicals, an in-vitro oxygen radical assay was used. The assay was run in quadruplicate to perfect the concentrations of controls as well as test the diluents (phosphate buffered saline (PBS) and DMSO) in which the DHEA and its derivatives were dissolved. The positive controls used were homocysteine and ascorbic acid (Vitamin C). The results of replicate experiments indicated that PBS and DMSO did not affect the light emission from luminol (the chosen chemiluminescent indicator) when it reacted with the oxygen radical given off by hydrogen peroxide. However, when diluted luminol was pre-incubated with DHEA at 100 μg/ml, the light emission was reduced by 20%; 7 hydroxy isoandrosterone reduced the luminol reaction by 15%; the 7 hydroxy DHEA did not cause any reduction of luminol in the assay. These results indicated that both DHEA and 7 hydroxy isoandrosterone are free radical scavengers.

Example 8

Chemical Alterations in the Skins of Neonatal Male Sprague-Dawley Rats

DHEA and the derivative compounds of DHEA (the 7 hydroxy derivative and 7 hydroxy-isoandrosterone) modified the elastin and collagen contents of neonatal rat skin when applied twice daily over a 30 day period at a concentration of 0.5% in a suitable carrier.

Collagen and elastin contents were measured on dry, defatted, hair-free skin samples. Collagen contents were assessed through hydroxyproline evaluations in hydrolyzed, 0.1N hot sodium hydroxide extracts. Elastin contents were measured by HPLC evaluation of the contents of thermolysin-produced peptides in digests of the hot sodium hydroxide residue. Controls were both shaven and unshaven, the shaven receiving only the carrier twice daily.

Using five animals per group, the results indicated that in the treated groups, collagen was increased by 24% for the 7 hydroxy derivative and the 7 hydroxy-isoandrosterone whereas DHEA itself induced a decrease of 16%. Elastin contents were increased by all the compounds (28% for DHEA, 30% for the 7 hydroxy derivative and the 7 hydroxy-isoandrosterone). In these studies, statistical analysis of variance was significant at an alpha level of 0.01. Similar to the histological observations, these chemistries were reversible. Collagen and elastin contents returned to near normal levels after cessation of treatment for 30 days.

Example 9

Apoptosis Effects

Effects of 3β,7α-dihydroxy-5-androstene-17-one (7α-hydroxy-DHEA) and of 3β,7α-dihydroxy-5 α-androstane-17-one (7α-hydroxy-ISOA) on the cellular apoptosis induced by glucocorticoids was measured. The thymus of a C57BL/6 mouse, age four weeks, was removed. Culture of the thymocytes was carried out for 6 hours in a RPMI 1640 medium and in the presence or in the absence of the steroid tested. The apoptosis (fragmentation of the DNA) was measured by flow cytometry after staining of the cells with propidium iodide. The apoptotic phenomenon was controlled by electrophoresis of the DNA developed by ethidium bromide according to the traditional technique (observation of ladders of 200 pairs of bases). The results reported in Table VII below were obtained:

TABLE VII

| Steroids in the Medium (in 10 ml of ethanol) | Apoptotic Cells (%) |
| --- | --- |
| Ethanol alone | 41.5 |
| Dexamethasone $10^{-6}$ M | 72.7 |
| Dexamethasone $10^{-6}$ M + DHEA $10^{-6}$ M | 39.0 |

TABLE VII-continued

| Steroids in the Medium (in 10 ml of ethanol) | Apoptotic Cells (%) |
| --- | --- |
| Dexamethasone $10^{-6}$ M + 7α hydroxy-DHEA $10^{-6}$ M | 58.8 |
| Dexamethasone $10^{-6}$ M + 7α hydroxy-ISOA $10^{-6}$ M | 72.0 |
| Dexamethasone $10^{-5}$ M | 73.5 |
| Dexamethasone $10^{-5}$ M + DHEA $10^{-5}$ M | 51.4 |
| Dexamethasone $10^{-5}$ M + 7α hydroxy-DHEA $10^{-5}$ M | 48.6 |
| Dexamethasone $10^{-5}$ M + 7α hydroxy-ISOA $10^{-5}$ M | 46.3 |

The data show that the 7α-hydroxysteroids may have an anti-apoptotic effect that opposes that of dexamethasone on the T cells of mice. The effect at $10^{-5}$ M is greater than that of the steroid precursor (DHEA or dehydro-epiandrosterone or 3β-hydroxy-5-androstene-17-one).

Example 10

Effects on Cell Viability

The effects of 3β,7α-dihydroxy-5-androstene-17-one (7α-hydroxy-DHEA) on the viability of human keratinocytes in culture was examined.

Human keratinocytes were obtained from surgical items and were cultivated in a monolayer until preconfluence. The 7α-hydroxy-DHEA was administered to these cultures at various concentrations in ethanolic solution (10%), each concentration being tested eight times. Controls were carried out with ethanol alone (10%). After twenty-four hours, the viability of the keratinocytes was measured by testing with MTT (3-(4,5-dimethylthiazol-2-yl)-2,5 diphenyl tetrazolium bromide) where the mitochondrial dehydrogenase succinate converts the MTT into blue crystals of formazan soluble in DMSO (Mosmann, J. Immunol. Methods 65: 55-63, 1983). The results of the tests on the viability of the keratinocytes are reported in Table VIII below. The cellular viability is calculated according to the formula:

% viability=$DO_{540}$ product×100/$DO_{540}$ control.

A value greater than 100 indicates a product that encourages cellular viability.

TABLE VIII

| Steroids in the Medium (in 10 ml of ethanol) | Viability of the Keratinocytes (%) |
| --- | --- |
| 10% ethanol alone (control) | 100 |
| 7α-hydroxy-DHEA $10^{-4}$ M | 124 ± 10 |
| 7α-hydroxy-DHEA $5 \times 10^{-5}$ M | 111 ± 7 |
| 7α-hydroxy-DHEA $10^{-5}$ M | 119 ± 7 |
| 7α-hydroxy-DHEA $5 \times 10^{-6}$ M | 147 ± 9 |
| 7α-hydroxy-DHEA $10^{-6}$ M | 154 ± 6 |
| 7α-hydroxy-DHEA $5 \times 10^{-7}$ M | 139 ± 3 |
| 7α-hydroxy-DHEA $10^{-7}$ M | 147 ± 5 |
| 7α-hydroxy-DHEA $10^{-8}$ M | 127 ± 3 |

The data indicate that 7α-hydroxy-DHEA increases viability of human keratinocytes at concentrations between $10^{-4}$ M and $10^{-8}$ M, the maximum (viability increases of between 54% and 39%) being obtained between $5 \times 10^{-6}$ M and $10^{-7}$ M. Furthermore, no cytotoxicity was observed. Other comparative tests have demonstrated that the precursor DHEA had no effect (100±5).

Example 11

Effects on Cell Proliferation

The effects of 3β,7α-dihydroxy-5-androstene-17-one (7α-hydroxy-DHEA) on the proliferation of human fibroblasts in culture was tested.

Cultures of human fibroblasts (from a 32 year old woman) were seeded on twenty-four site plates at the rate of 50,000 cells per site in a standard culture medium (DMEM, gentamycine, amphotericine B, penicillin, L-glutamine, 10% SVF). The tests were carried out on four series of three sites. After twenty-four hours, the fibroblasts adhered to the support and three series were treated with 7α-hydroxy-DHEA at concentrations of $10^{-6}$ M, $5\times10^{-6}$ M and $10^{-7}$ M. The fourth series only contained the vector (ethanol). The media were renewed daily, and at ninety-six hours (seventy-two hours of test contact with the 7α-hydroxy-DHEA), the fibroblasts were counted on a Malassez cell in the presence of blue trypan.

The results of the effects on the proliferation of fibroblasts are reported in Table IX below.

TABLE IX

| Steroids in the Medium | Number of Fibroblasts | Increase in Viability (%) |
|---|---|---|
| Control | 190,667 ± 6,766 | — |
| 7α-hydroxy-DHEA $10^{-7}$ M | 230,667 ± 8,511 | +21 |
| 7α-hydroxy-DHEA $10^{-6}$ M | 268,000 ± 27,154 | +41 |
| 7α-hydroxy-DHEA $5 \times 10^{-6}$ M | 258,667 ± 3,351 | +36 |

The results indicate that, under these experimental conditions, the treatment of fibroblasts by 7α-hydroxy-DHEA at $10^{-7}$ M, $10^{-6}$ M and $5\times10^{-6}$ M increases the cellular proliferation by respectively 21%, 41% and 36% with respect to the untreated control fibroblasts.

Example 12

Anti-Radical Effects

The anti-radical effects of 30β,7α-dihydroxy-5-androstene-17-one (7α-hydroxy-DHEA) on a suspension of human keratinocytes was tested.

Keratinocytes from a healthy donor (25 year old woman) were cultivated to the subconfluent stage in a specific medium (KGM) for the proliferation of keratinocytes. The suspensions obtained were split up, in triplicate, into four series, of which three were irradiated for thirty minutes with a lamp emitting UVA so as to speed up the production of free radicals. Among the three irradiated series, one contained Vitamins C and E (0.7%) and was used as a protection reference; one contained 7α-hydroxy-DHEA at $10^{-6}$ M and the last served as a control. Table X below reports on the measurement of the anti-radical effects.

The free radicals produced generated lipid peroxides which are measured by chemiluminescence (Belghmi et al. J Biolum. Chemilum. 2: 113-119, 1982). The effectiveness of the 7α-hydroxy-DHEA was calculated on the basis of non-irradiated controls and the protection reference.

TABLE X

| Keratinocytes | Chemiluminescence | Effectiveness |
|---|---|---|
| Non irradiated control | 2,529 ± 153 | — |
| Irradiated controls | 427,750 ± 137,322 | — |
| Irradiated + 0.7% Vit. C + E | 2,970 ± 288 | 100% |
| Irradiated + 7α-hydroxy-DHEA $10^{-6}$ | 44,164 ± 13,303 | 90% |

Under the conditions of this study, in vitro anti-radical effectiveness of 7α-hydroxy-DHEA at $10^{-6}$ M is 90%. 7α-hydroxy-DHEA can be considered as a good anti-radical product.

Example 13

Effects of Peptides and Retin A

It has been found that, in combination with or in conjunction with the peptides or peptide-like compounds, an improvement in elasticity is detected when using a tretinoin.

In these studies, a Cutometer (Courage & Khazaka, Germany) was used to quantify skin elasticity. The Cutometer's vacuum probe was placed perpendicular to the skin surface to contact the skin and measure its elasticity. This device then generates data which includes several readings: immediate skin deformation, delayed distention, final deformation, and immediate retraction. The Cutometer SEM 5751, (available from Courage & Khazaka, Germany) allows relatively objective determination of elasticity of the skin (See Skin & Allergy News 30 (2): 18, 1999). For details on the Cutometer and the testing methods cited herein one is directed to the text Bioengineering of the Skin Methods and Instrumentation (1995 Catalog Number 8374, ISBN: 0849383749, as well as the 1998 version which are both hereby incorporated by reference thereto in their entirety).

A number of volunteers were treated with the hydrolyzed elastin peptides (as described herein, SEQ IDs 1-41) at a 2% weight concentration, versus a group of volunteers who used Retin A (actually RENOVA®) first and then applied the 2% hydrolyzed elastin product. The RENOVA® used was a tretinoin emollient cream at a 0.05% weight concentration. It contained the active tretinoin (a retinoid) in an emollient cream base. Tretinoin includes RENOVA® at a concentration of 0.05% wt/wt in a water in oil emulsion formulation consisting of light mineral oil, NF, sorbitol solution USP; hydroxyoctacosanyl hydroxystearate; methoxy PEG-22/dodecyl glycol copolymer; PEG45/dodecyl glycol copolymer; stearoxytrimethylane and stearyl alcohol; dimethicone 50 cs ; methylparaben, NF; acetate disodium, USP; quaternium-15; butylated hydroxytoluene, NF; citric acid monohydrate, USP, fragrance ; and purified water, USP.

The hydrolyzed elastin peptides (SEQ IDs 1-41) in a 2% by weight concentration were applied to various test subjects. Over a two-month period, the R2 was between 24% and 23% increase and the R7 was 31%. Results obtained by using a 0.05% by weight RENOVA® formulation followed by application of the 2% hydrolyzed elastin peptide cream of the present invention. In these patients the elasticity, as measured by R2 and R7, doubled on average.

Table XI illustrates samplings over 3 separate intervals (separated by approximately one month) with 5 separate patients. For the example subject identified as 45 (bg) there was a consistent and dramatic increase in elasticity. Table XI is shown below.

TABLE XI

|  | Interval | 1 Month | | 2 Month | | 3 Month | |
|---|---|---|---|---|---|---|---|
|  |  | 1 Pull | 3 Pulls | 1 Pull | 3 Pulls | 1 Pull | 3 Pulls |
| Subject: 41 (th) Fitz: III Gender: F-48 | R2 (Gross) | +55% | +62% | +54% | +64% | +57% | +62% |
|  | R5 (Net) | +70% | +72% | +66% | +77% | +55% | +68% |
|  | R7 (Portion) | +60% | +64% | +56% | +61% | +49% | +61% |
| Subject: 42 (vb) Fitz: IV Gender: F-54 | R2 (Gross) | +75% | +63% | +76% | +76% | +85% | +68% |
|  | *L Cheek | N/A |  | +78% | +40%* | +82% | +65% |
|  | R5 (Net) | +86% | +81% | +77% | +82% | +86% | +81% |
|  | *L Cheek | N/A |  | +88% | +10%* | +88% | +81% |
|  | R7 (Portion) | +76% | +67% | +68% | +76% | +82% | +73% |
|  | *L Cheek | N/A |  | +81% | +29% | +83% | +70% |
| Subject: 41 (ce) Fitz: III Gender: F-41 | R2 (Gross) | +68% | +67% | +73% | +67% | +60% | +69% |
|  | *L Cheek | N/A |  | +26% | +17%* | +9% | +4% |
|  | R5 (Net) | +71% | +77% | +86% | +89% | +74% | +68% |
|  | *L Cheek | N/A |  | +39%* | +50%* | −18% | −14% |
|  | R7 (Portion) | +64% | +64% | +74% | +72% | +67% | +58% |
|  | *L Cheek | N/A |  | +26%* | +39%* | +2% | +2% |
| Subject: 44 (ph) Fitz: II Gender: F-50 | R2 (Gross) | +55% | +65% | +65% | +65% | +42% | +59% |
|  | *L Cheek | N/A |  |  |  |  |  |
|  | R5 (Net) | +77% | +79% | +81% | +79% | +76% | +84% |
|  | *L Cheek | N/A |  |  |  |  |  |
|  | R7 (Portion) | +65% | +66% | +53% | +66% | +60% | +71% |
|  | *L Cheek | N/A |  |  |  |  |  |
| Subject: 45 (bg) Fitz: III Gender: F-52 | R2 (Gross) | +15% | −23% | +2% | +8% | +1% | +3% |
|  |  |  |  |  | **+16% |  | **+22% |
|  |  |  |  |  |  |  | **+5% |
|  | R5 (Net) |  | +6% | −28% | +25% | +26% | +38% | +4% |
|  |  |  |  |  | **+42% |  | **+25% |
|  |  |  |  |  |  |  | **−20% |
|  | R7 (Portion) | +6% | −28% | −9% | −16% | +1% | −22% |
|  |  |  |  |  | **+17% |  | ***+8% |
|  |  |  |  |  |  |  | *−10% |

*2$^{nd}$ Biopsy taken L. Cheek
**Monthly interval variances showed a wide range of + and − readings
Note:
Cutometer readings represent one and three pulls. One pull = total elasticity; three pulls = fatigue and recovery.

Figure 4:
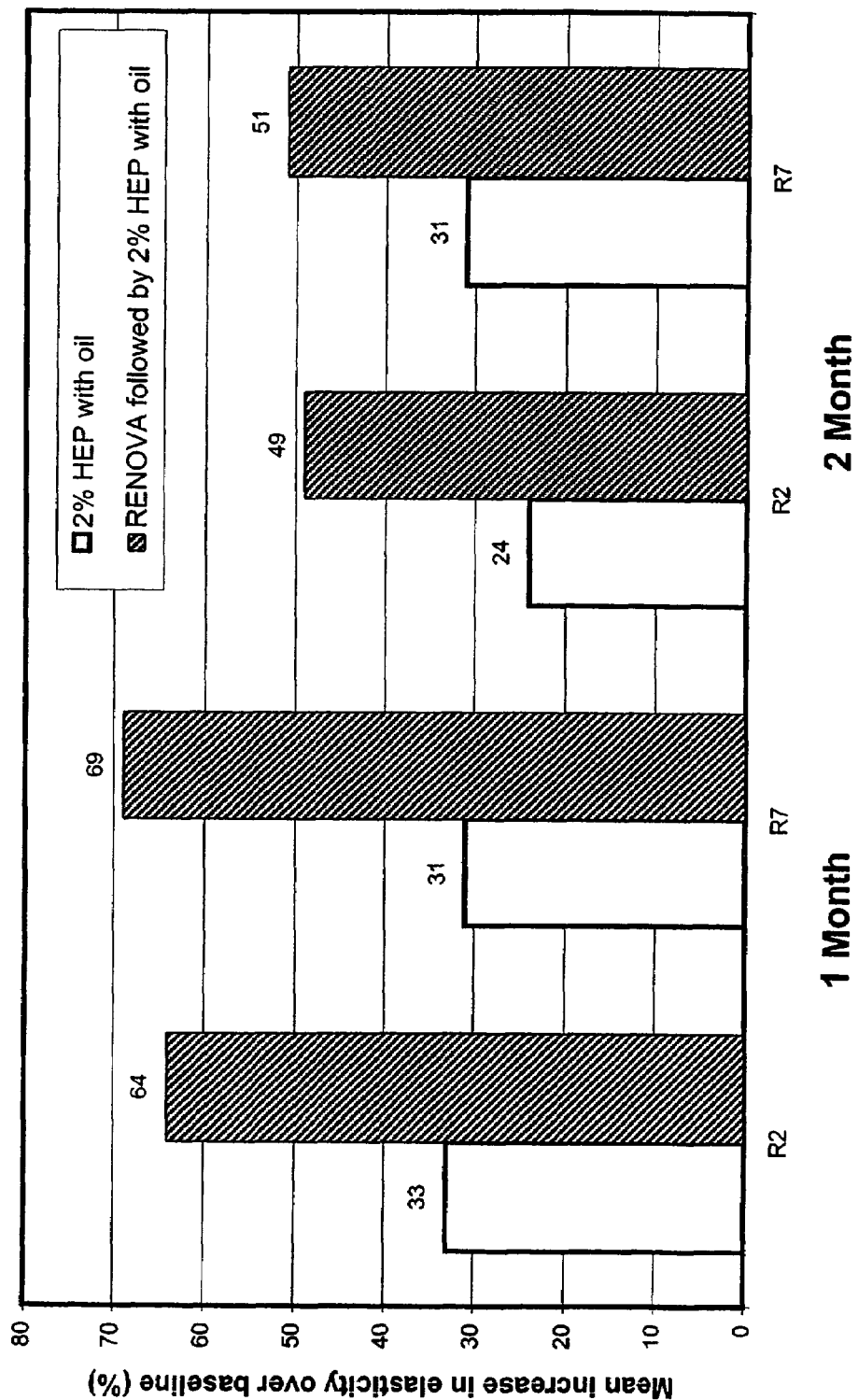
FIG. 4 illustrates the results of an example experiment in a bar graph, showing measurement of elasticity of the skin by a Cutometer for skin treated with a peptide composition or a peptide composition plus RENOVA®.

FIG. 4 and Table XI illustrate the results obtained when using various embodiments. All readings on the Cutometer have been taken in Mode 1, which is constant negative pressure: 5 seconds on, 5 seconds off. The pull of three curves indicates the fatigue and recovery of the skin, while one pull indicates the elasticity of the curve. Group 4 studies include both one and three pulls. R2=gross elasticity. It is represented by Ua/Uf which indicates the total pull and relaxation of the skin under negative pressure. R5=net elasticity. It is represented by Ur/Ue which indicates the perpendicular pull and relaxation of the skin under negative pressure. R7=portion elasticity. It is represented by Ur/Uf and is indicative of the portion of elasticity relative to the entire curve. Based upon the Cutometer readings and the in vivo analysis, it appears that the peptides of the present invention stimulate or simulate elasticity of the tissue.

While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. For example, the compounds can be administered via many alternative drug delivery vehicles known in the art and the peptides can be derived from digestion of elastin or by amino acid sequencing (either solid state or liquid), as well as from over-expression in a bacterial system. Modification (either chemical or enzymatic) of the basic sequences described herein are also within the purview of the present invention. Therefore the disclosed sequences may be modified to include this residue at either the amino or carboxyl ends of the peptides. The sequences may also be chemically modified to increase their activity (e.g., amidation of the carboxyl terminus portion of a sequence). Computational chemistry may be used to predict structure-function relationships, and compounds thus predicted and synthesized may mimic the structure and function of a particular peptide or peptide-like compound disclosed herein and may be utilized. The peptides may be chemically modified to increase their activity. Accordingly, all such variances should be viewed as being within the scope of the present invention as set forth in the claims below.

What is claimed is:

1. A composition useful in treating mammalian tissue, said composition being comprised of SEQ ID 12.

2. The composition of claim 1, wherein the peptide is soluble in an aqueous solution.

3. The composition of claim 2, wherein the peptide is at a therapeutically effective concentration.

4. The composition of claim 1, wherein the peptide is formed by digestion of elastin with thermolysin.

5. The composition of claim 3, wherein the therapeutically effective concentration is a range of about 0.0002% to about 90%.

6. The composition of claim 5, wherein the therapeutically effective concentration is in the range of about 0.5% to about 10%.

7. The composition of claim 1, wherein the composition is a cosmetic preparation.

8. The composition of claim 7, wherein the cosmetic preparation is selected from an emulsion, a lotion, a spray, an aerosol, a powder, an ointment, a cream or a foam.

9. The composition of claim 1, wherein the tissue being treated is a blood vessel.

10. The composition of claim 1, wherein the composition is used for treating a condition selected from hypertension, coronary heart disease, arteriosclerosis, angina, coronary thrombosis, chronic obstructive pulmonary disease, and restenosis post angioplasty.

11. The composition of claim 1, wherein the composition further comprises at least one steroid.

12. A composition useful in improving tissue turgor, said composition being comprised of SEQ ID 12.

13. The composition of claim 12, wherein the composition further includes a pharmaceutical delivery system.

14. The composition of claim 12, wherein the peptide is derived from elastin.

15. The composition of claim 14, wherein the peptide is derived from animal tissue.

16. The composition of claim 13, wherein the pharmaceutical delivery system is a topical delivery system.

17. The composition of claim 16, wherein the pharmaceutical delivery system is a subcutaneous delivery system.

18. The composition of claim 16, wherein the topical delivery system is selected from a cosmetic preparation, a powder, an emulsion, a lotion, a spray, an ointment, an aerosol, a cream or a foam.

19. The composition of claim 12, wherein the composition further comprises at least one steroid.

20. A pharmaceutical composition comprised of SEQ ID 12.

21. The pharmaceutical composition of claim 20, wherein application of the composition to a patient results in neovascularization.

22. The pharmaceutical composition of claim 20, wherein application of the composition to a patient results in angiogenesis.

23. The pharmaceutical composition of claim 20, wherein the composition further comprises at least one steroid.

24. The pharmaceutical composition of claim 20, wherein the composition is formulated as a topical preparation.

25. The pharmaceutical composition of claim 24, wherein the composition is formulated as a preparation selected from a cosmetic preparation, a powder, an emulsion, a lotion, a spray, an ointment, an aerosol, a cream or a foam.

* * * * *